United States Patent
Diaz et al.

[19]

[11] Patent Number: 5,890,128
[45] Date of Patent: Mar. 30, 1999

[54] PERSONALIZED HAND HELD CALORIE COMPUTER (ECC)

[76] Inventors: H. Benjamin Diaz; M. Inez Genera, both of P. O. Box 294, Brea, Calif. 92622

[21] Appl. No.: 610,380

[22] Filed: Mar. 4, 1996

[51] Int. Cl.$^6$ ..................................................... G06F 17/00
[52] U.S. Cl. .............................. 705/2; 128/921; 364/400; 364/700
[58] Field of Search ........................... 128/921; 364/400, 364/700, 709.03, 709.12; 705/2

[56] References Cited

U.S. PATENT DOCUMENTS

| | | | |
|---|---|---|---|
| 4,100,401 | 7/1978 | Tutt et al. | 235/92 T |
| 4,159,416 | 6/1979 | Brejnik et al. | 235/92 MT |
| 4,192,000 | 3/1980 | Lipsey | 364/415 |
| 4,244,020 | 1/1981 | Ratcliff | 364/413 |
| 4,321,674 | 3/1982 | Krames et al. | 364/413 |
| 4,380,802 | 4/1983 | Segar et al. | 364/900 |
| 4,575,804 | 3/1986 | Ratcliff | 364/715 |
| 4,686,624 | 8/1987 | Blum et al. | 364/415 |
| 4,796,182 | 1/1989 | Duboff | 364/413.29 |
| 4,894,793 | 1/1990 | Ikemoto et al. | 364/709.03 |
| 5,233,520 | 8/1993 | Kretsch et al. | 364/413.29 |
| 5,412,564 | 5/1995 | Ecer | 600/300 |
| 5,704,350 | 11/1998 | Williams, III | 600/300 |

*Primary Examiner*—Edward R. Cosimano

[57] ABSTRACT

A novel hand held individually customized interactive integrated circuit device for nutrition and exercise management. Featuring built in Random Access Memory (RAM) Storage of extensive food lists with associated caloric and fat contents. The device also incorporates RAM storage of exercises with associated activity caloric values or rates. The basic unit utilizes the individual's personal characteristics such as sex, age, weight, height, frame size, life style and goals with programmed calculations to derive optimum suggested weight, metabolic rate, daily caloric/fat intake targets, exercise targets and exercise/daily calorie burning rates. The personalized hand held calorie computer tracks daily and historical individual caloric input/output, fat input, and weight which can be viewed in the form of charts and graphs. Alarms are provided in a variety of tones, sounds, and tunes which alert the individual to breach of prescribed optimum daily caloric/fat intake or signal special events such as times for medication, special eating intervals, and appointments. Additionally, it can be used with optional wireless activity sensing and odometer attachments already available in the market to automatically track/deduct burned calories from total daily caloric intake when walking, running, riding a bicycle, or performing other activities. The device is intended for use by individuals interested in increasing, decreasing or maintaining their body weight for personal or medical reasons. Optional medical programs take into consideration special dieting, medication and exercise requirements of patients with diabetes, high cholesterol, heart ailments, hypoglycemia and other diseases. Confidentiality is assured by use of a Personal Identification Number (PIN) which is selected and changed at will by the individual user. The device will be available in various languages. Other functions include a four function calculator and a clock/calendar.

15 Claims, 17 Drawing Sheets

PERSONALIZED HAND HELD CALORIE COMPUTER (ECC)

BACKGROUND—FIELD OF INVENTION

This invention relates generally to hand held computers and, more specifically, to a totally new way such a device with food and exercise listings in its memory is programmed to utilize personal characteristics and activity sensing devices to individually custom tailor physical and dietary parameters such as optimum weight, daily/exercise calorie burning rates, daily caloric/fat input targets, and caloric inputs/outputs in a comprehensive nutrition and exercise management system.

BACKGROUND—DESCRIPTION OF PRIOR ART

More people everywhere are trying to gain control of their weight for personal and medical reasons. Medical science has made tremendous progress in the area of understanding human weight control and more importantly the health hazards brought on by not maintaining a diet which is more relevant to individual life styles and physical needs. Unfortunately, this wealth of new found knowledge has succeeded only in creating an information overload to the populace in general.

Anyone desiring to control his/her weight has to find out his/her metabolic rate at rest, consult long lists of exercise caloric burning rates, calculate his/her caloric burning rates for each exercise using the listed data and his/her metabolic rate, consult cumbersome books listing calories and fat content of foods, document this data daily and manually track this data on an on going basis.

Furthermore, it has been proven that sudden and significant changes in diet activates the body's natural resistance to weight changes by adjusting its metabolic rate ultimately resulting in the individual regaining any weight losses before the body's metabolism settles down. This is a serious source of frustration for chronic dieters.

Some devices now available to the public simply allow the individual to add calories taken in or deduct calories burned during exercises based on information derived from food/exercise lists, odometer readings, pedometer readings and exercise machine time/calorie counters. Others have limited internal lists in which as many food items as possible are bunched into caloric groups. The user selects these ambiguous food groups through the complex manipulation of switches to enter the caloric amounts of foods eaten, which are then totaled. These methods have several inherent problems in common. First, and most important is that they are extremely complicated to use. Second, the devices' accuracy depend on the individual's ability to refer to and interpret complex lists of food and exercises or his/her calculating abilities. Third, the individual has to manually track the historical data. Fourth, the individual does not get scientifically derived weight, diet and exercise targets. Fifth, they assume that everyone's goal is to lose weight. Sixth, they do not take into consideration medically driven dieting, athletic dieting, weight gain dieting etc. Seventh, they do not establish targets. Eighth, they do not let the user know how they are doing over a period of time longer than a day. Ninth, they do not utilize a gradual increase/decrease in daily caloric targets to prevent the body from making metabolic rate changes to maintain its weight. Finally, they do not provide alarms to let the user know when they are overshooting their daily targets.

There is software available for PCs which take a scientific approach, establish target weights, diet and daily exercises and which have extensive food and exercise lists to choose from for anyone wishing to lose weight. Although this approach is moving more in the right direction it still has four drawbacks for business people and active people on the go: First, even laptop computers are too cumbersome and costly for daily use. Second, the programs are not interactive so the user still has to document the most basic exercises and later enter them into the PC. Third, they only deal with weight loss diets. Fourth, they do not address weight gain nor medically driven diets.

U.S. Pat. Nos. 4,100,401 to Eugene F. Tutt and Rita C. Tutt and 4,159,416 to Carl J. Brajnik and William T. Whitlow are in the form of wristwatches capable of adding numbers derived from manual lists or charts indicative of caloric intake and holding these totals. The former deducts numbers obtained from exercise lists or derived from complicated calculations from the running caloric count. The latter converts the wearers pulse to calories expended which is in turn deducted from the total calories. The pulse conversion to calories has proven to be an extremely inaccurate means of calculating caloric output. U.S. Pat. No. 4,192,000 to Elmer P. Lipsey is a belt or pocket worn device which accurately measures the individual's caloric output and continuously accumulates expended calories. This invention, however, does not track input calories. U.S. Pat. Nos. 4,244,020 (1981), 4,321,674 (1982), and 4,575,804 (1986) are hand held calculators which utilize complicated coded keys and special coded food reference lists to enter the individual's caloric input. U.S. Pat. No. 4,686,624 to Dominique Blum is a portable device with a stored food listing which allows a direct food to caloric input conversion and accumulation without referring to reference lists intended for use only in medical applications. It does not track output calories. U.S. Pat. No. 4,796,182 to Gary Duboff is a hand held device which starts with the individual's daily caloric budget and the user deducts caloric input by selecting buttons bearing food categories which convert to calories consumed. This device has the advantage of not using an external look-up list. The general food item entry approach, however, yields highly inaccurate results because many foods and dishes are combinations of food items which should be considered in that context. A cheeseburger for instance contains cheese, beef, bread, lettuce, onions and tomatoes. It is much simpler and accurate to enter this cheeseburger as a food item having a certain amount of calories and fat. This device does not track output calories. U.S. Pat. No. 4,894,793 to Yutaka Ikemoto and Akiyoshi Yamashita is a hand held calculator with a food list in an internal memory which allows direct conversion to calories consumed by selecting and entering the food items. This device tracks only consumed fat and calories. U.S. Pat. No. 5,233,520 to Mary J. Kretsch, Moira A. Gunn and Alice K. Fong is an interactive desk top PC system consisting of a centralized computer and various desk top computers at individuals' homes used for diet surveying purposes only. This system has food lists in memory and tracks calories consumed, but it is not a hand held device and it does not track output calories. U.S. Pat. No. 4,380,802 to Richard B. Segar and Lewis C. Marascalco uses a modified calculator to store coded caloric quantities representing foods consumed which can be retrieved by the user by first referring to coded food listings and then using the codes to retrieve the data from the device (col.2, ll. 40 to 48). Thus, Segar's invention requiring external coded food listings is not self contained as is applicants' present invention with the capability of storing an excess of 2000 food items and their caloric/fat contents which can be easily retrieved by the user on demand without the use of any external references. In addition, the prior art (Segar et al) also has coded numbers roughly representing coded caloric burn rates which the user also retrieves by referring to external coded activity listings (col. 2, ll. 32 to 39). The applicants' present invention is self contained in this regard also automatically providing the appropriate physical activity caloric burn rate when the user selects the activity from the exercise menu without the use of any external references. Segar requires that the user constantly change activity codes, start the activity and stop the activity throughout the day in order to acquire an accurate caloric output (col. 4, l. 54 to col. 5, l. 5). This is highly problematic for two reasons. First, the individual has to constantly stop and look up activities and charts. Second, if the user forgets to change an activity it is difficult to correct that day's caloric output since the device continues to run. Unlike Segar, the applicants' present invention automatically calculates the users daily calories burned during daily routine activities based on the individual's physical characteristics and normal activity level. Therefore, the user need only start and stop higher levels of activities such as running or riding a bicycle. This results in a more accurate and much more convenient means of tracking the individual's daily calories burned. U.S. Pat. No. 5,412,564 to Gunes M. Ecer uses a smart card which can be electronically updated to record an individuals caloric intake at check-out counters, restaurants and grocery stores (col. 2, ll. 55 to 66). His system requires a centralized computer an IC card read write unit, display units, printers, a bar code reader, and a keyboard (FIG. 1) at each store or restaurant in order to sense calories of food products purchased. When a card user pays for food products he presents his smart card to the checker who inserts it into an IC card read/write unit. The computer senses the information from the smart card, adds data from the bar code reader representing food purchased to the user's daily totals and provides an updated print out for the user (FIG. 2). This prior art requires a special set-up at every store and restaurant that the user frequents. It does not provide a means of updating at the users residence, when invited to dinner at someone else's home, when purchasing food at restaurants and stores not equipped to update the card or when eating lunch at work. Furthermore, groceries purchased at grocery stores would be evenly divided as consumed by the whole family, presumably, at the time of purchase. In reality groceries purchased are not eaten in equal portions by all family members i.e. baby formula is purchased with groceries but only eaten by babies. In addition food purchased at a grocery store is eaten over an indefinite period of time, i.e. leftovers are eaten several days after a meal. This prior art does not explain how it would handle groceries bought for one or two week periods or how to account for food eaten by dinner guests. For these reasons, Ecer's invention is clearly not functional. The applicants' invention overcomes all these obstacles because it is totally self contained allowing real time updating of stored data of calories and fat content of exact portions of foods as they are consumed. In order for this prior (Ecer) art to establish maximum daily and fat levels, the user must visit a doctor every time his physical characteristics change to obtain this data to be input into his smart card (col. 4, ll. 28 to 48). The applicants solved this problem by incorporating formulas into the present invention which derive weight targets, daily caloric targets, daily fat targets and establish individual caloric burn rates. Ecer's invention provides a print out containing the individual's nutritional status only when he makes a purchase at a store or restaurant equipped to process the smart card. (col. 3, ll. 38 to 39). The applicants' invention, on the other hand, uses a built in random access memory and an easy to use retrieval means to present the user's daily and historical caloric input, fat input and caloric output as well as corresponding targets on a display means on demand.

Table 1-1 compares the features of the prior art discussed above with the features of our invention. As the table clearly shows with the exception of U.S. Pat. No. 5,894,520 to Mary J. Kretsch, Moira A. Gunn and Alice K. Fong which has no features in common with our invention, all the other prior art in the chart has at least 2 features in common with our

TABLE 1-1

| | | | | | | | | | PRIOR ART | | | | | | |
|---|---|---|---|---|---|---|---|---|---|---|---|---|---|---|---|
| | | I N V E N T | 4 1 0 0 4 0 | 4 1 5 9 4 1 | 4 1 9 2 0 0 | 4 2 4 4 0 2 | 4 3 2 1 6 7 | 4 3 8 0 8 0 | 4 5 7 5 8 0 | 4 6 8 6 6 2 | 4 7 9 6 1 8 | 4 8 9 4 7 9 | 5 4 1 2 5 6 | 5 2 3 3 5 2 |
| Comparison table of our invention's features to prior art's features. FEATURES | O U R | I O N | 1 | 6 | 0 | 0 | 4 | 2 | 4 | 4 | 2 | 3 | 4 | 0 |
| Hand Held Computer | ● | | | | | | | | | | | | | |
| Food Listing In RAM | ● | | | | | | | | ● | | ● | | 7 | |
| Calories per Item of Food in RAM | ● | | | | ● | ● | ● | ● | ● | ● | ● | | 7 | |
| Fat Content per Item of Food in RAM | ● | | | | | | ● | | | | ● | | 7 | |
| Daily Input Calories Target Calculated Using Personal Data | ● | | | | | | ● | | | | ● | ● | 8 | |
| Fat Input Target Calculated Using Personal Data | ● | | | | | | | | | | ● | | 8 | |
| Daily Caloric Input Totaled | ● | | ● | ● | | ● | ● | ● | ● | ● | | ● | ● | ● |
| Daily Fat Input Totaled | ● | | | | | | ● | | | | ● | | ● | ● |
| Daily Caloric Output Totaled | ● | | ● | ● | ● | | | ● | | | | | | |
| Alarms Indicating Caloric/fat Targets Have Been Exceeded | ● | | | | | | 1 | ● | | | ● | 1 | | |
| Historical Listing of Daily Caloric/Fat Input | ● | | | | | | | | | 1 | | | ● | |
| Historical Listing of Daily Caloric Totals (Input Cals Burned Cals) | ● | | | | | | | | | | | | | |
| Historical Graph of Daily Caloric Inputs | ● | | | | | | | | | | | | | |
| Weight Target Calculated Using Personal Data | ● | | | | | | | | | | | | | |
| Historical Listing of Weekly Weight Totals | ● | | | | | | | | | | | | | |
| Historical Graph of Weekly Weight Totals | ● | | | | | | | | | | | | | |

TABLE 1-1-continued

| Comparison table of our invention's features to prior art's features. FEATURES | OUR INVENTION | PRIOR ART | | | | | | | | | | | |
|---|---|---|---|---|---|---|---|---|---|---|---|---|---|
| | | 4,100,401 | 4,159,416 | 4,192,000 | 4,244,020 | 4,321,674 | 4,380,802 | 4,575,804 | 4,686,624 | 4,796,182 | 4,894,793 | 5,412,564 | 5,233,520 |
| Direct Input of Activity Sensor & Conversion to Burned Calories | ● | | 2 | 3 | | | | | | | | | |
| Personal Data Used to Calculate Targets & Burned Calories | ● | 6 | | 4 | | | 4 | | | | | | |
| Password Protection | ● | | | | | | | | | | | | |
| Menu Driven Computer Access | ● | | | | | | | | | | ● | | |
| Screen With Plurality of Lines | ● | | | | | | | | | | | | |
| Special Programming for Medically Required Diets | ● | | | | | | | | ● | | ● | | |
| Available in Various Languages | ● | | | | | | | | | | | 5 | |
| Full Function Calculator | ● | | | | | | ● | | ● | | ● | | |
| Clock and Calendar | ● | ● | ● | | | | | | | | | | 7 |
| Alarm Clock | ● | ● | ● | | | | | | | | | | |
| Carbohydrate Totals | | | | | | ● | ● | ● | | | ● | | |
| Coded Keys and Requires Separate Listing of Foods | | | | | | ● | ● | ● | ● | ● | | | |
| Utilizes General Food Catagories | | | | | | | | | | ● | | | |
| Utilizes a Scale to Weigh and Convert Food to Calories | | | | | | ● | | | ● | | ● | | |
| Described as a Portable Apparatus | | | | | | | | | | ● | | ● | ● |
| Described as a Hand Held Calculator | | | | | | ● | ● | | ● | | ● | ● | |
| Described as a Chronometer | | ● | ● | | | | | | | | | | |
| Described as a Device | | | | | | | ● | ● | | ● | | | |
| Described as a Desk Top Personal Computer | | | | | | ● | | ● | | | | | ● |

NOTES:
1. Tracks calories only.
2. Uses pulse rate to derive burned calories.
3. Uses vertical motion sensor to derive burned calories.
4. Calculates burned calories only.
5. English and Japanese only.
6. Must refer to a metabolic rate chart, enter metabolic rate into device, refer to activity hourly burning rate charts and enter this data into device each time a new activity is started.
7. Kept in centralized computer connected to check out systems.
8. Doctor must provide or user selects preferance.

invention. However, none of the prior art in the table share all the features with our invention. The features incorporated in our invention are necessary to provide a confidential, convenient, interactive, easy to use, hand held device which provides a user with truly real time comprehensive caloric/fat targets and historical data directly tied to the individual's physical characteristics, metabolism, way of life, physical activities, and eating habits. This comprehensive information in turn allows the user to make conscious well informed health changes related to physical activities and dietary routine as often as desired to increase, decrease or maintain body weight.

OBJECTS AND ADVANTAGES

Accordingly, besides the objects and advantages of the hand held easy to use interactive personal nutrition and exercise management computer described in our above patent, several objects and advantages of the present invention are:

(a) to provide a personalized hand held computer with an extensive list of foods and their respective calorie and fat content for review in deciding daily diet or for entry before or after consumption;

(b) to provide a personalized hand held calorie computer with an extensive list of exercises and their respective calorie burning properties for review or for entry when performed;

(c) to provide a personalized hand held calorie computer that will accept a user's name, phone number, address, age, sex, height, weight, frame size, lifestyle and goals to customize the program to the individual;

(d) to provide a personalized hand held calorie computer that will use personal profile data to calculate the user's optimum weight;

(e) to provide a personalized hand held calorie computer that will use personal profile data to calculate the user's daily caloric input target;

(f) to provide a personalized hand held calorie computer that will use personal profile data to calculate daily caloric output;

(g) to provide a personalized hand held calorie computer that will use personal profile data to calculate daily individual calorie burning characteristics;

(h) to provide a personalized hand held calorie computer that will use personal profile data to calculate individual exercise calorie burning rates;

(i) to provide an interactive personalized hand held calorie computer that automatically calculates calories burned while walking, running, playing tennis, playing racquet/hand ball, playing golf or performing aerobic exercise by using optional activity sensing attachments;

(j) to provide an interactive personalized hand held calorie computer that automatically calculates calories burned while riding a bicycle by using optional odometer attachments;

(k) to provide a personalized hand held calorie computer that calculates daily graduated caloric targets the first predetermined number of days of dieting to prevent metabolic rate changes which counteract the dieters efforts;

(l) to provide a personalized hand held calorie computer that generates tone or musical alarms when the user exceeds or nears his/her daily caloric/fat targets;

(m) to provide a personalized hand held calorie computer that generates tone and musical alarms with messages for personal, medical and dietary reasons;

(n) to provide a personalized hand held calorie computer that holds a predetermined number of days over seven days of historical weight data in the form of charts and graphs;

(o) to provide a personalized hand held calorie computer that holds a predetermined number of days over seven days of historical caloric input data in the form of charts and graphs;

(p) to provide a personalized hand held calorie computer that holds a predetermined number of days over seven days of historical caloric output data in the form of charts and graphs;

(q) to provide a personalized hand held calorie computer that holds a predetermined number of days over seven days of historical fat input data in the form of charts and graphs;

(r) to provide a personalized hand held calorie computer with total privacy through the use of a PIN which may be changed at will;

(s) to provide a personalized hand held calorie computer with special medical diet, exercise and medication programming for users suffering from diabetes, high cholesterol, heart ailments hypoglycemia and other diseases;

(t) to provide a personalized hand held calorie computer with special programming for athletes such as but not restricted to long distance runners, weight lifters, and body builders;

(u) to provide a personalized hand held calorie computer with programming in English, Spanish, German, Italian, French and eventually other languages.

Further objects and advantages are to provide a personalized hand held calorie computer which allows the user to confidentially plan, record and track caloric and fat inputs and outputs on a daily, weekly and monthly basis without performing complicated mathematical computations to derive caloric burning rates, caloric data and or referring to cumbersome books containing long lists of food and exercise caloric values.

DRAWING FIGURES

In the drawings, closely related figures have the same number but different alphabetic suffixes.

REFERENCE NUMERALS IN DRAWINGS

Figure 1:
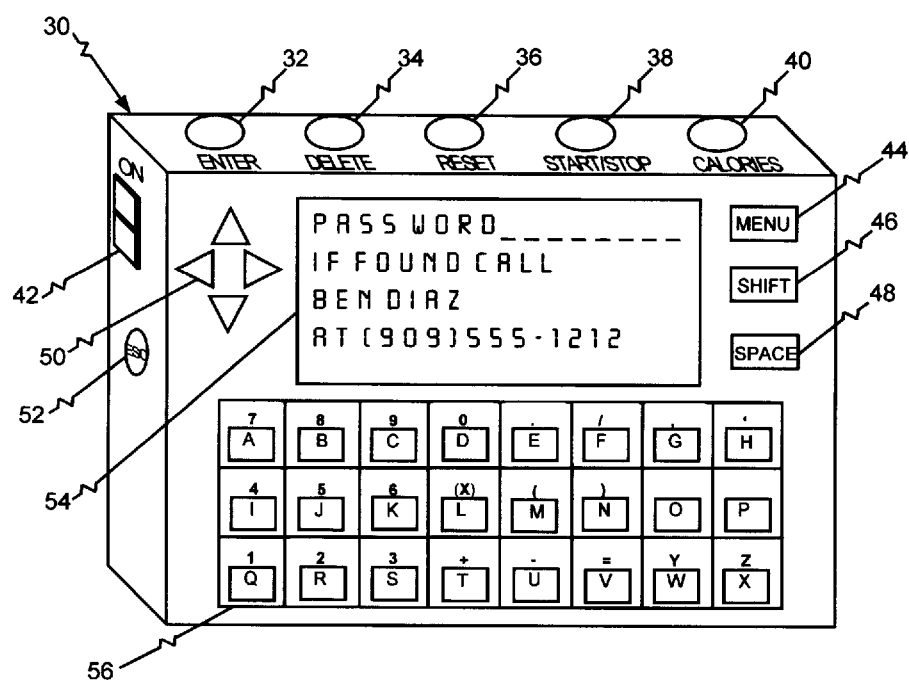
FIG. 1 is a perspective view of our uniquely novel personal hand held calorie computer showing the LCD display, keyboard, scrolling arrows, main menu switch, the shift switch, the space switch, the enter switch, the delete switch, the reset switch, the start/stop switch the calories switch, the power switch and the esc switch.

Drawing Reference Numerals Worksheet
PART NAME

| | |
|---|---|
| 30 | Hand held computer case |
| 32 | Enter button |
| 34 | Delete button |
| 36 | Reset button |
| 38 | Start/Stop button |
| 40 | Calories button |
| 42 | On/Off button |
| 44 | Menu button |
| 46 | Shift button |
| 48 | Space button |
| 50 | Scroll buttons |
| 52 | Esc button |
| 54 | Screen |
| 56 | Keyboard |
| 58 | Setup Menu screen 1 |
| 60 | Date/Time selection in Setup Menu |
| 61 | Clock Generator |
| 62 | Action, key in date and time |
| 63 | Receiver |
| 64 | Data in RAM - date and time |
| 66 | Your profile selection in Setup Menu |
| 68 | Action, key in your profile data |
| 70 | Action, press menu button |
| 72 | Action, key in your PIN |
| 74 | Data in RAM - personal data |
| 76 | First screen |
| 78 | Total daily output and target calculations |
| 80 | Password selection Setup Menu |
| 82 | Action, key in old and new password |
| 84 | Suggested weight calculations |
| 86 | Data in RAM - password |

Drawing Reference Numerals Worksheet
PART NAME

Figure 4:
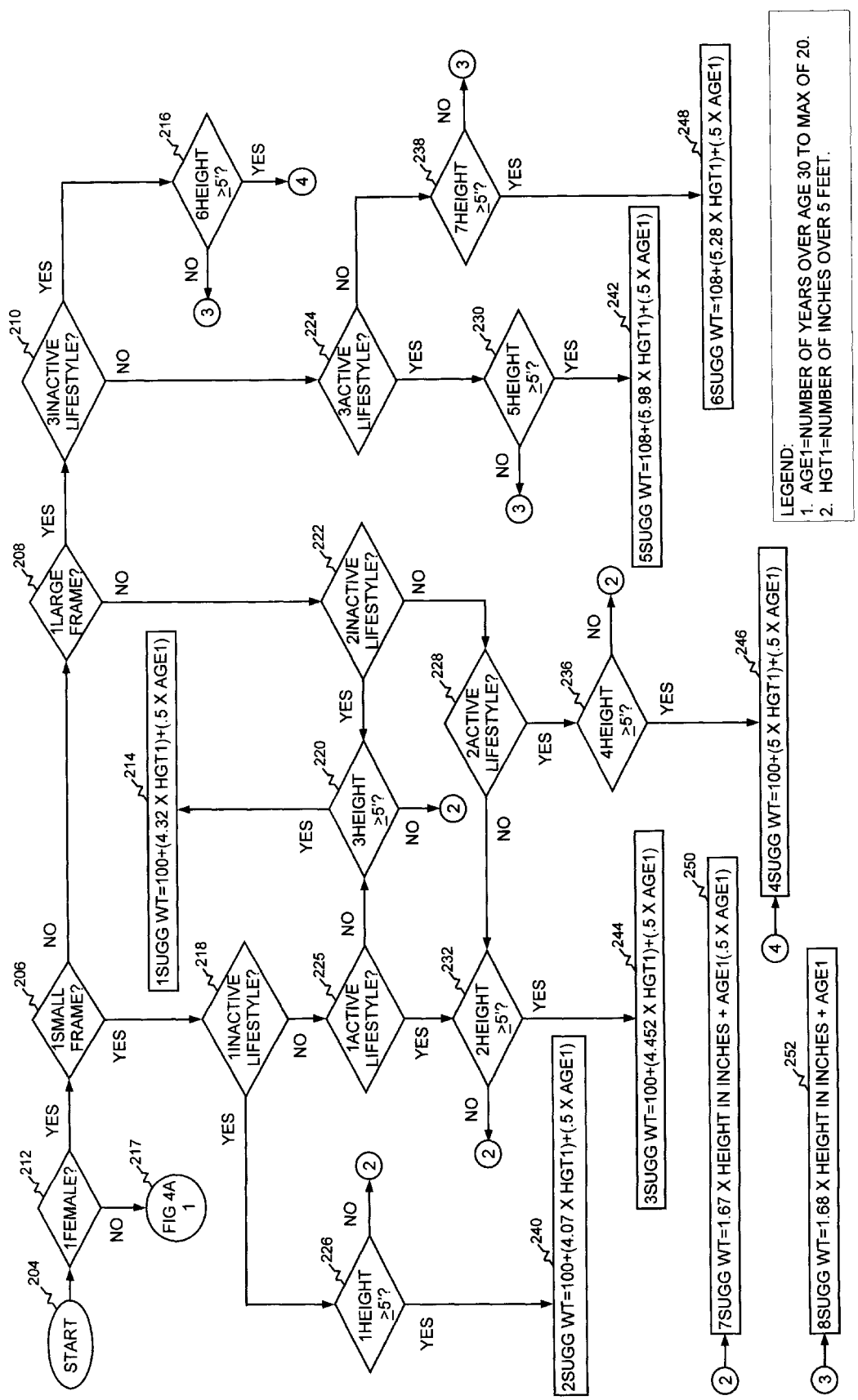
FIG. 4 is a flowchart showing the steps and calculations utilized in deriving women's suggested weight.
Figure 4A:
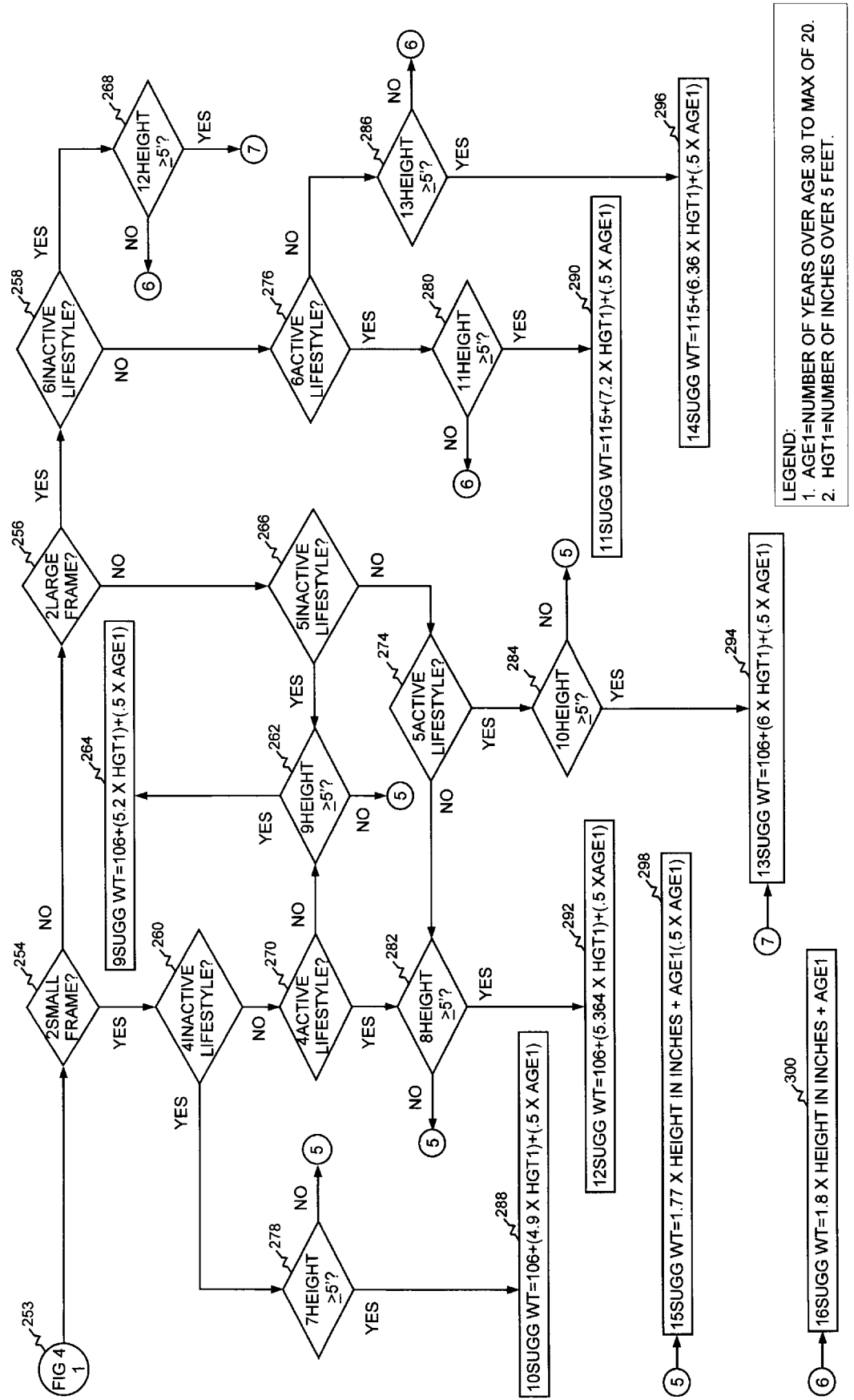
FIG. 4A is a flowchart showing the steps and calculations utilized in deriving men's suggested weight.

| | |
|---|---|
| 88 | Password comparison |
| 90 | Main Menu 1 (setup, food, exercise) |
| 92 | Alarms selection of Setup Menu |
| 94 | Action, key in alarm date, time, message, and select sound |
| 96 | Message to screen |
| 98 | Data in RAM - alarm date, time, message, and sound selection |
| 100 | Date and time comparison |
| 102 | Food selection of Main Menu |
| 104 | Action, select food item |
| 106 | Sound generation and speaker |
| 108 | Action, key in number of servings |
| 110 | Activity sensor or timer input |
| 112 | Data in RAM food item, calories, fat, and serving size |
| 114 | Exercise selection of Main Menu |
| 116 | Action, select activity and activity rate |
| 118 | Action, key in exercise time |
| 120 | Manual or automatic selection |
| 122 | Data in RAM - Exercise, rates, and time |
| 124 | Total calories selection in Main Menu |
| 126 | Action, select data to view |
| 128 | Data in RAM - history date, weight and target |
| 130 | Data in RAM - Today's totals (intake calories/fat, output/calories, total calories/fat, and target calories/fat) |
| 134 | Data in RAM-History Menu List (calories/fat, exercise, & daily total calories) |
| 136 | Data in RAM - History Totals (date, intake cals/fat, output cals, target cals/fat) |
| 138 | Data in RAM- History Menu Graph (calories, exercise, & weight graph) |
| 144 | Date and time screen |
| 146 | Sex, Birthdate, and Height screen |
| 150 | Frame screen, (small, medium, large) |
| 152 | Weight screen |
| 154 | Lifestyle screen, (inactive, semi-active, active) |
| 156 | Present daily calorie intake screen |
| 158 | Name, address screen |
| 162 | Setup Menu screen 2, alarms |
| 164 | Password screen, (old, new) |
| 166 | Recurring alarm screen |
| 168 | Target screen, (met, missed) |
| 170 | State, zip, phone screen |
| 172 | Food selection screen |
| 174 | One time alarm screen |
| 176 | Historical calories/fat screen |
| 178 | Goal screen, (lose, gain, or maintain weight) |
| 180 | Exercise selection screen |
| 182 | Todays total screen-calories/fat |
| 183 | Exercise screen |
| 184 | Food entry screen, (serving size) |
| 186 | Historical total calories screen |
| 188 | Main Menu screen 2-total calories |
| 190 | Historical output exercise screen |
| 192 | Historical calories, fat graph screen |
| 194 | Total Calories Menu screen |
| 200 | Calories graph |
| 201 | Historical weight graph screen |
| 204 | Start, suggested weight calculation flowchart, female |
| 206 | Decision, 1 small frame? |
| 208 | Decision, 1 large frame? |
| 210 | Decision, 3inactive lifestyle? (for large frame) |
| 212 | Decision, 1female? |
| 214 | 1Suggested weight |
| 216 | Decision, 6height? (inactive lifestyle large frame) |
| 217 | To FIG. 4A item 1 |
| 218 | Decision, 1inactive lifestyle? (small frame) |
| 220 | Decision, 3height? (small frame, semi-active) |
| 222 | Decision, 2inactive? (medium frame) |
| 224 | Decision, 3active lifestyle? (for large frame) |
| 225 | Decision, 1active lifestyle? (for small frame) |
| 226 | Decision, 1height? (for small frame inactive lifestyle) |
| 228 | Decision, 2active lifestyle? (for medium frame) |
| 230 | Decision, 5height? (for large frame) |
| 232 | Decision, 2height? (for small frame active lifestyle) |
| 236 | Decision, 4height? (for medium frame active lifestyle) |
| 238 | Decision, 7height? (for large frame active lifestyle) |
| 240 | 2Suggested weight |
| 242 | 5Suggested weight |
| 244 | 3Suggested weight |
| 246 | 4suggested weight |
| 248 | 6Suggested weight |
| 250 | 7Suggested weight |
| 252 | 8suggested weight |
| 253 | From FIG. 4 item 1 |
| 254 | Decision, 2small frame? (for male) |
| 256 | Decision, 2large frame? (for male) |
| 258 | Decision, 6inactive lifestyle? (for large frame male) |
| 260 | Decision, 4inactive lifestyle? (for small frame male) |
| 262 | Decision, 9height? (for small framed semi-active mate) |
| 264 | 9Suggested weight |
| 266 | Decision, 5inactive lifestyle? (for medium framed male) |
| 268 | Decision, 12height? (for inactive large framed male) |
| 270 | Decision, 4active lifestyle? (small framed male) |
| 274 | Decision, 5active lifestyle? (for medium framed male) |
| 276 | Decision, 6active lifestyle? (for large framed male) |
| 278 | Decision, 7height? (for small frame inactive lifestyle male) |
| 280 | Decision, 11height? (for large framed active lifestyle male) |
| 282 | Decision, 8height? (for small framed active lifestyle male) |
| 284 | Decision, 10height? (for medium framed active lifestyle male) |
| 286 | Decision, 13height? (for large framed active lifestyle male) |
| 288 | 10Suggested weight |
| 290 | 11Suggested weight |
| 292 | 12Suggested weight |
| 294 | 13Suggested weight |
| 296 | 14suggested weight |
| 298 | 15Suggested weight |
| 300 | 16Suggested weight |
| 301 | Start for Total Caloric Output Calculation |
| 302 | Decision, manual input? |

Drawing Reference Numerals Worksheet
PART NAME

Figure 5:
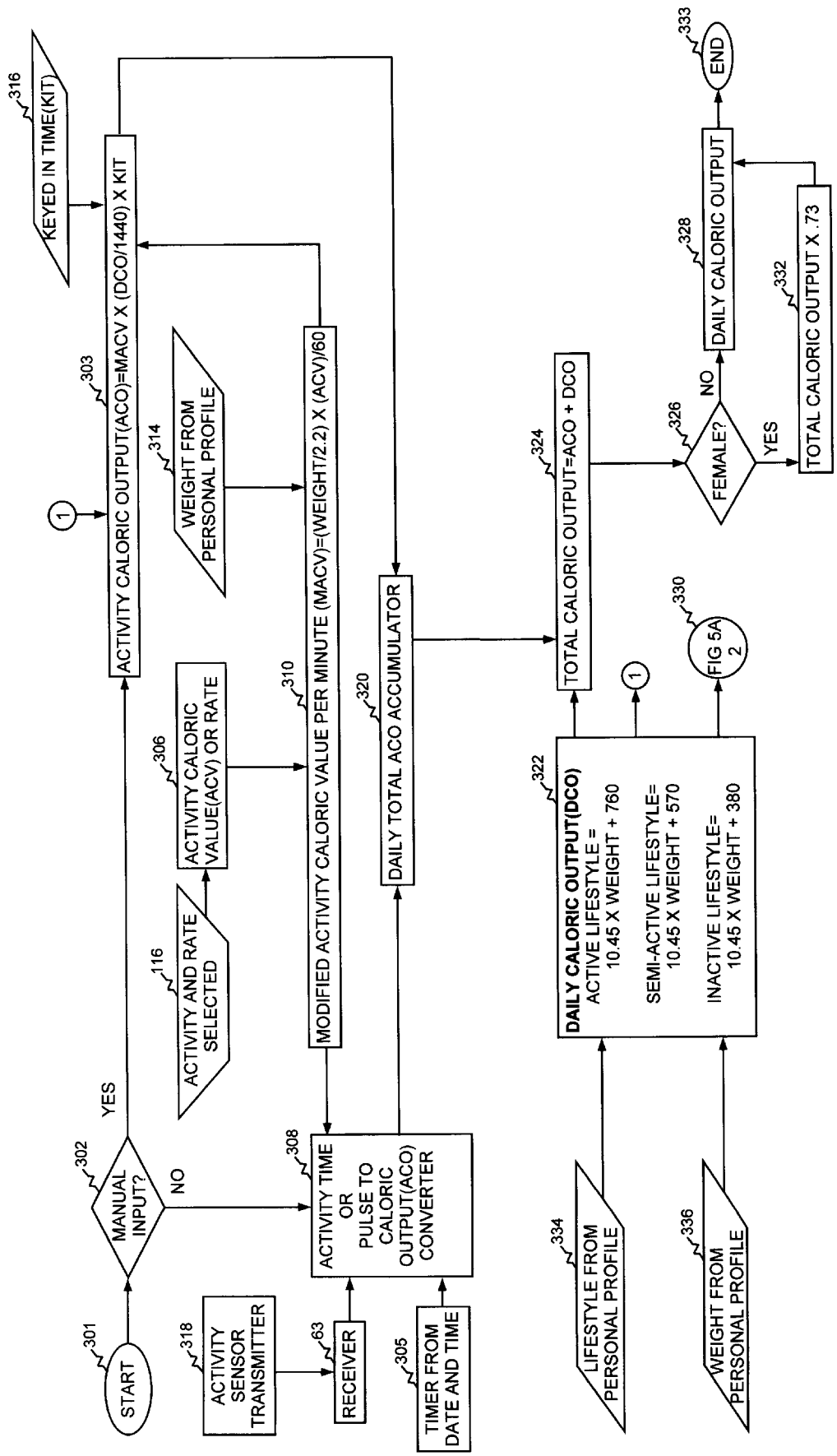
FIG. 5 is a flowchart showing the steps and calculations utilized in deriving the individual's total daily caloric output.
Figure 6:
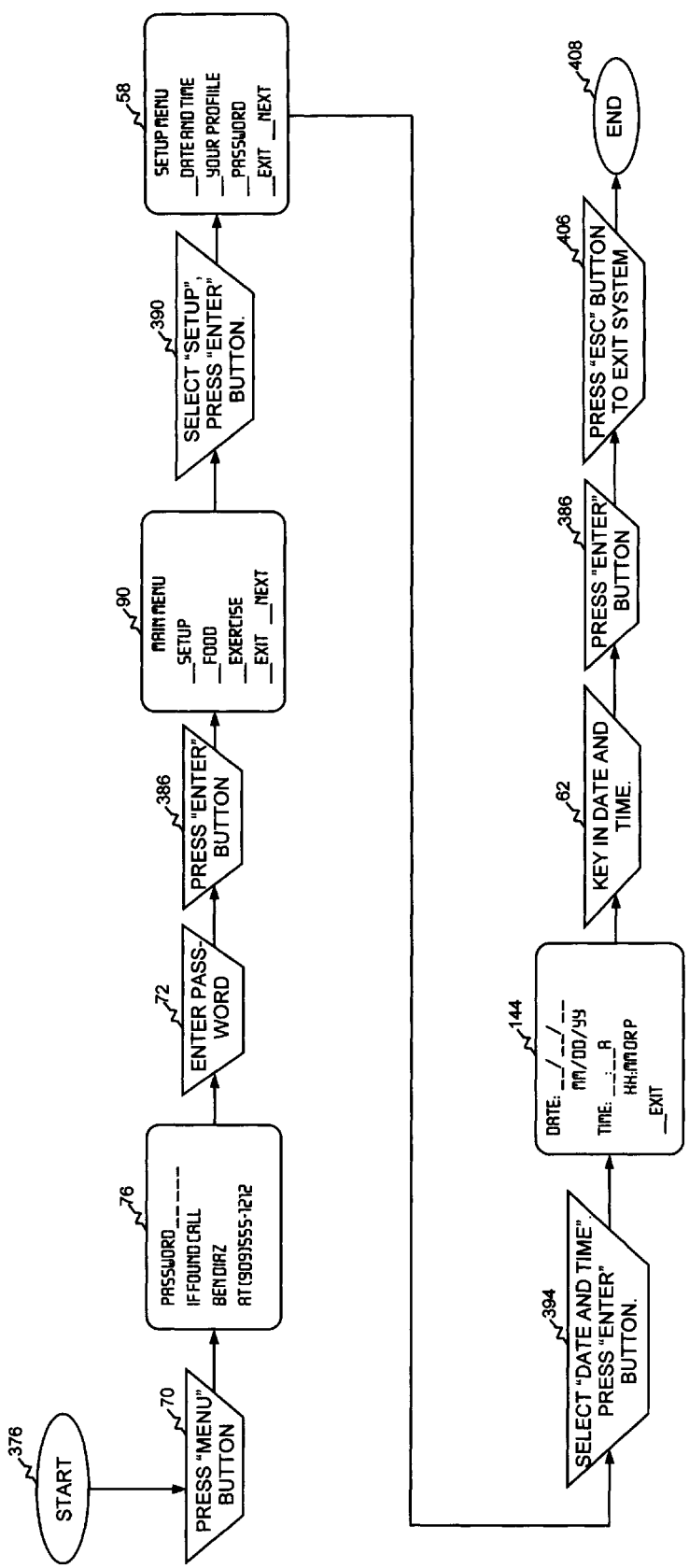
FIG. 6 is a flowchart showing the steps taken to set the date and time on the personal hand held calorie computer.
Figure 7:
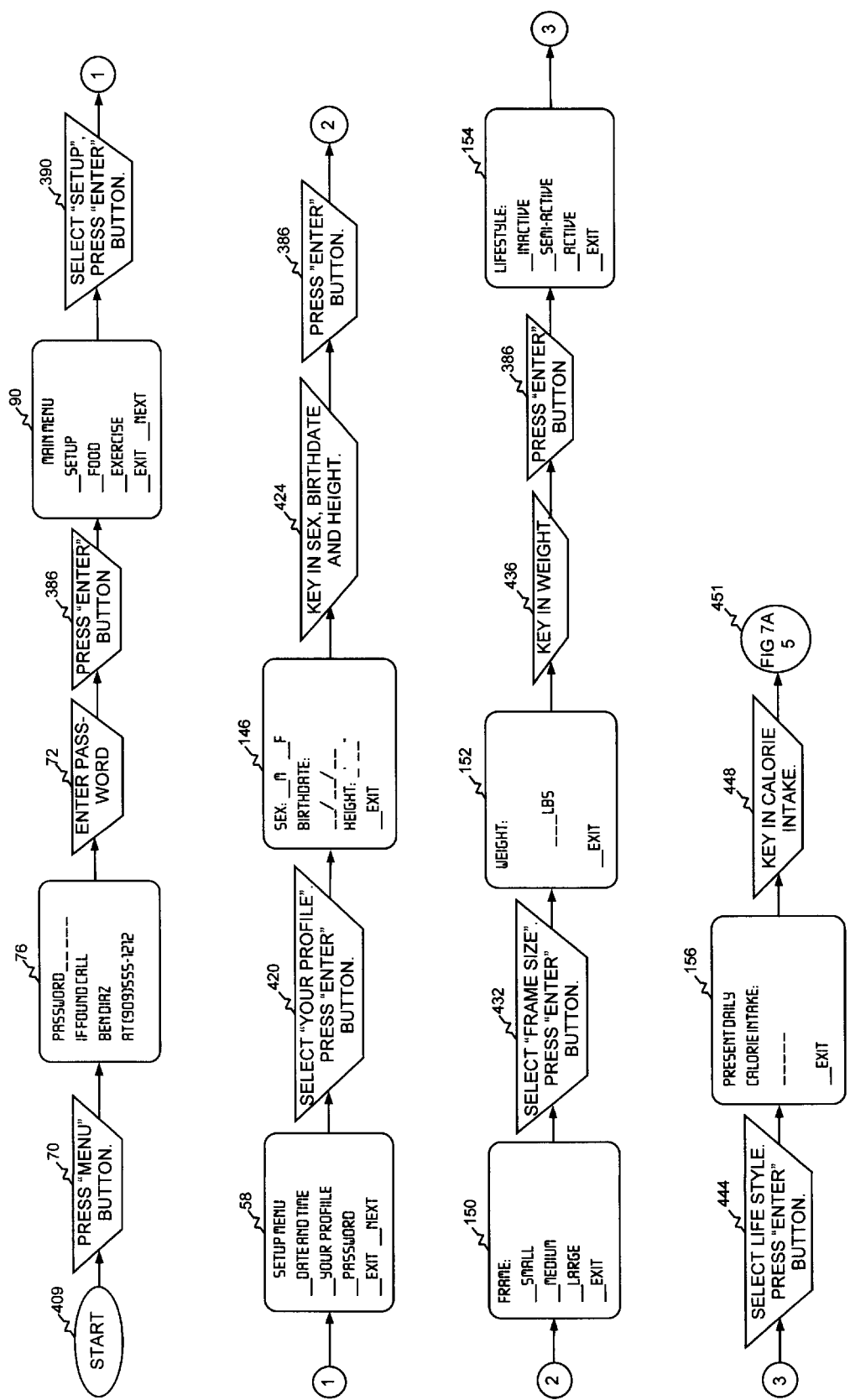
FIGS. 7 and 7A are flowcharts showing the steps taken to input the personal profile data into the hand held calorie computer.
Figure 7A:
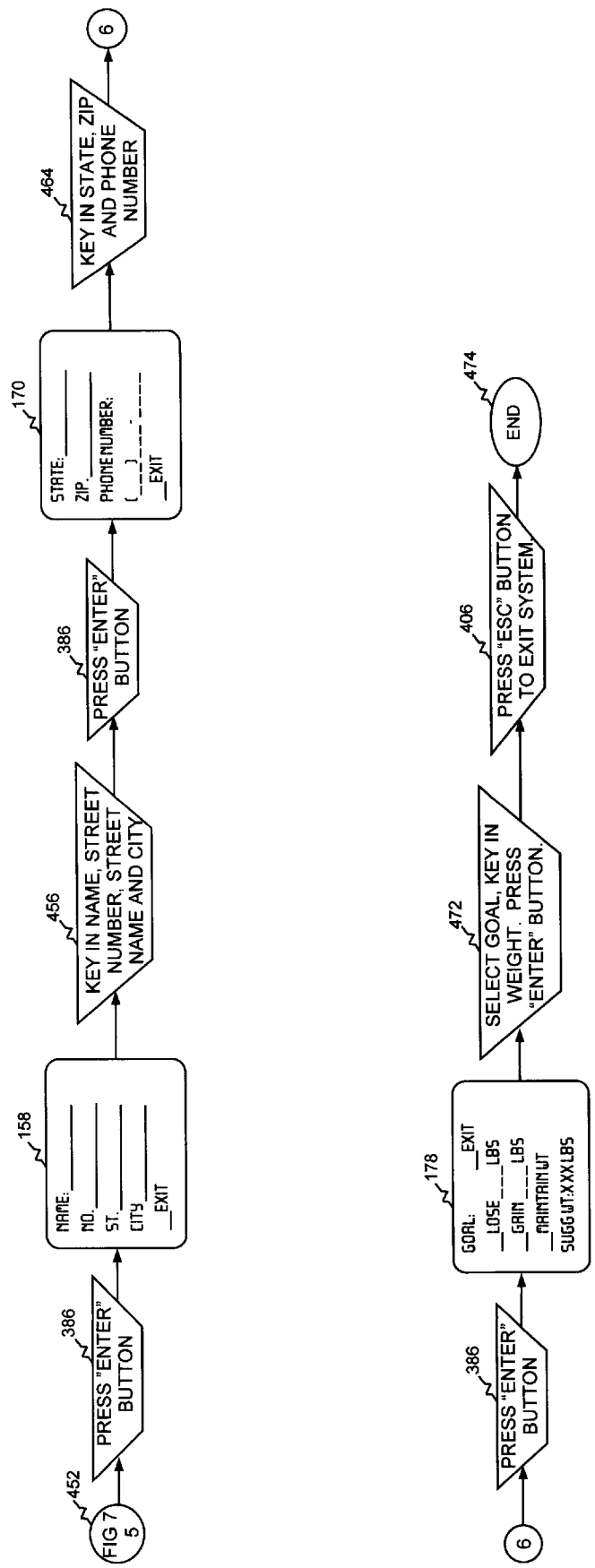
Figure 12:
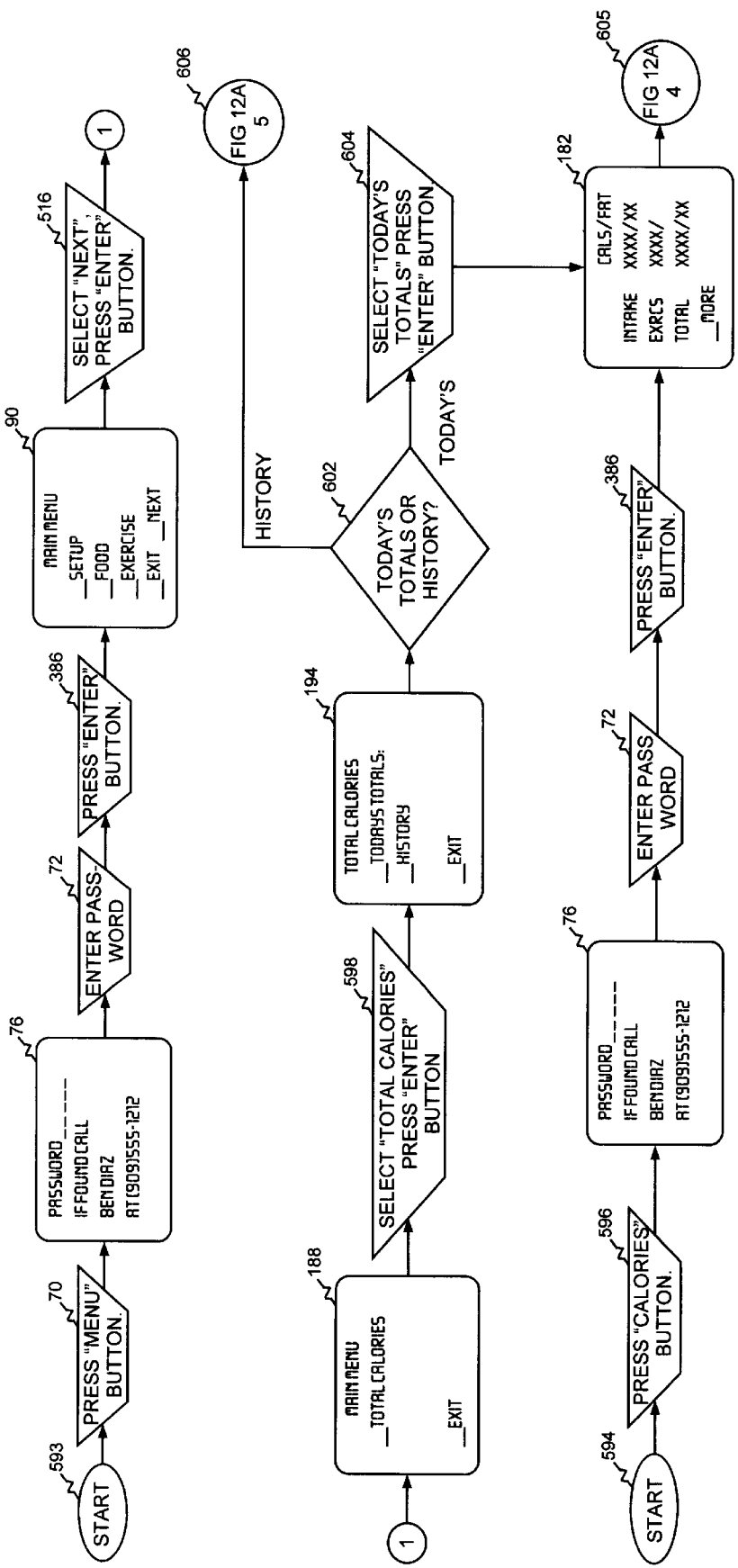
FIGS. 12, 12A and 12B are flowcharts showing the steps taken to view weight and caloric/fat historical charts and graphs in the personal hand held calorie computer.
Figure 12A:
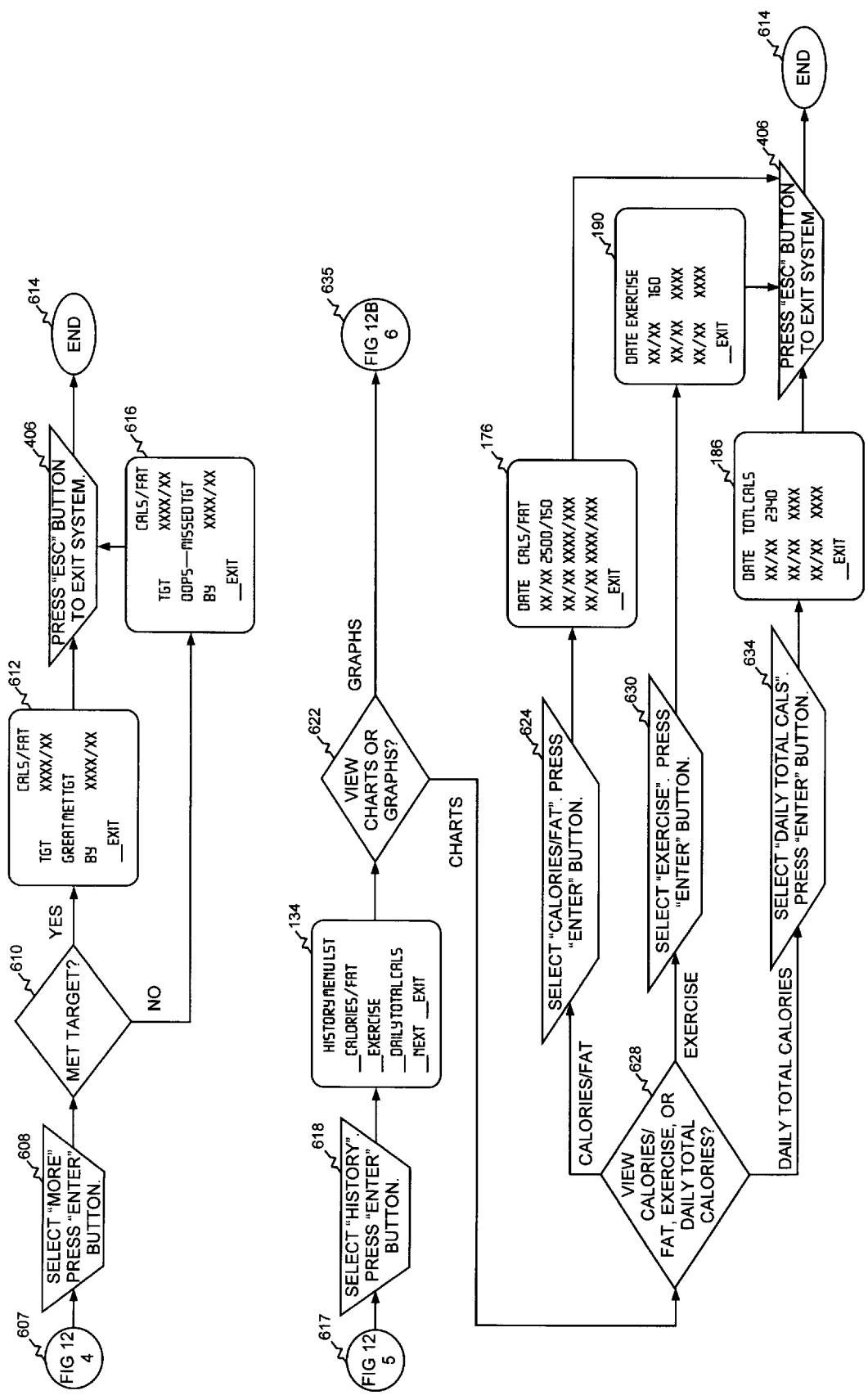

| | |
|---|---|
| 303 | Activity caloric output (ACO) calculation |
| 305 | Timer from date and time |
| 306 | Activity caloric value (ACV) or rate |
| 308 | Activity time or pulse to caloric output (ACO) converter |
| 310 | Modified activity caloric value per minute (MACV) calculation |
| 314 | Weight, from personal profile |
| 316 | Keyed in time (KIT) |
| 318 | Activity exercise sensor transmitter |
| 320 | Daily total ACO accumulator |
| 322 | Daily calorie output (DCO) calculation (by lifestyle) |
| 324 | Total caloric output |
| 326 | Decision, 2female (total cal output) |
| 328 | Daily caloric output |
| 330 | DCO To FIG. 5 item 2 |
| 332 | Total caloric output calculation for female |
| 333 | End of total caloric output calculation |
| 334 | Lifestyle from personal profile |
| 336 | Weight from personal profile |
| 337 | Daily caloric/fat target calculations, start |
| 338 | First date entered |
| 340 | Decision, is date = or < than 30 days? |
| 342 | Day counter |
| 344 | Day count calculation, calorie target modifier (CTM) |
| 348 | Change "present calorie intake" value to "daily calorie target" instruction |
| 350 | Present calorie intake from personal profile |
| 352 | Present calorie intake (PCI) |
| 354 | Caloric intake difference (CID) |
| 356 | Daily caloric output, calculation for females |
| 358 | Daily caloric target (DCT) |
| 360 | Daily adjustment calculation |
| 362 | Decision, 3female? (for daily calorie/fat targets) |
| 364 | Adjusted daily calorie target |
| 365 | End of daily cal/fat calculations |
| 366 | Input from FIG. 5, item 2 |
| 368 | Daily fat target, calculation |
| 370 | Decision, 4female? (for daily fat target) |
| 372 | Daily fat target calculation for female |
| 374 | Daily fat target register |
| 376 | Start setting date & time, flowchart (FIG. 6) |
| 386 | Action, press enter button |
| 390 | Action, select setup, press enter button |
| 394 | Action, select date and time, press enter button |
| 406 | Action, press ESC button to exit system |
| 408 | End of date & time flow chart |
| 409 | Start setting personal profile (FIG. 7) |
| 420 | Action, select "your profile" press enter button |
| 424 | Action, key in sex, birthdate, and height |
| 432 | Action, select "frame size" press enter button |
| 436 | Action, key in weight |
| 444 | Action, select life style, press enter button |
| 448 | Action, key in calorie intake |
| 451 | To FIG. 7A, item 5 |
| 452 | Input from FIG. 7 Item 5 |
| 456 | Action, key in street #, street name and city |
| 464 | Action, key in state, zip, and phone number |
| 472 | Action, select goal, key in weight, press enter button |
| 474 | End of setting personal profile flowchart |
| 475 | Start of setting password flowchart |
| 500 | Action, select "password", press enter button |
| 510 | End of setting password flowchart |
| 514 | Start setting alarms flowchart |
| 516 | Action, select "next", main menu press enter button |
| 520 | Action, select "alarms" press enter button |
| 524 | Decision, type of alarm? |
| 532 | End of setting of alarms flowchart |
| 534 | Action, select "next" (type of alarm) press enter button |
| 538 | Action, key in recurring time, start time, message, and press enter button |
| 540 | Start of food-view and enter flowchart |
| 542 | Action, select "food", press enter button |
| 546 | Key in name of food or use up-down arrows to find food name |
| 560 | Decision, want to enter or view more food? |
| 562 | End of food view and enter |
| 563 | Start of exercise, view & enter |
| 564 | Action, select "exercise" press enter button |
| 568 | Action, key in name of exercise or use up/down arrows to find exercise name and press enter button |
| 572 | Action, select speed of exercise |
| 574 | Decision, use exercise sensor or timer? |
| 580 | Action, key in P for pedometer, O for odometer or T for timer |
| 586 | Action, press start/stop button once to start exercise |
| 588 | Decision, do you want to view or enter other exercises? |
| 590 | End of exercise-view and enter |
| 592 | Action, press start/stop button once to stop exercise |
| 593 | Start of total calories flowchart conventional method |
| 594 | Start of total calories flowchart using calories button |
| 596 | Action, press calories button |
| 598 | Action, select "total calories", press enter button |
| 602 | Decision, todays totals or history? |
| 604 | Action, select "todays total", press enter button |
| 605 | To FIG. 12A item 4 |
| 606 | Output to FIG. 12A item 5 |
| 607 | Input from FIG. 12 item 4 |
| 608 | Action, select "more", press enter button |
| 610 | Decision, met target? |
| 612 | Target screen for targets met |
| 614 | End of total calories |
| 616 | Target screen for targets missed |
| 617 | Input from FIG. 12 item 5 |
| 618 | Select history, press enter button |
| 622 | Decision, view charts or graphs |
| 624 | Select calories/fat, press enter button |
| 628 | Decision view calories/fat, exercise, or daily total calories |
| 630 | Action, select "exercise", press enter button |
| 634 | Action, select "daily total calories", |

-continued

Drawing Reference Numerals Worksheet
PART NAME

Figure 12B:
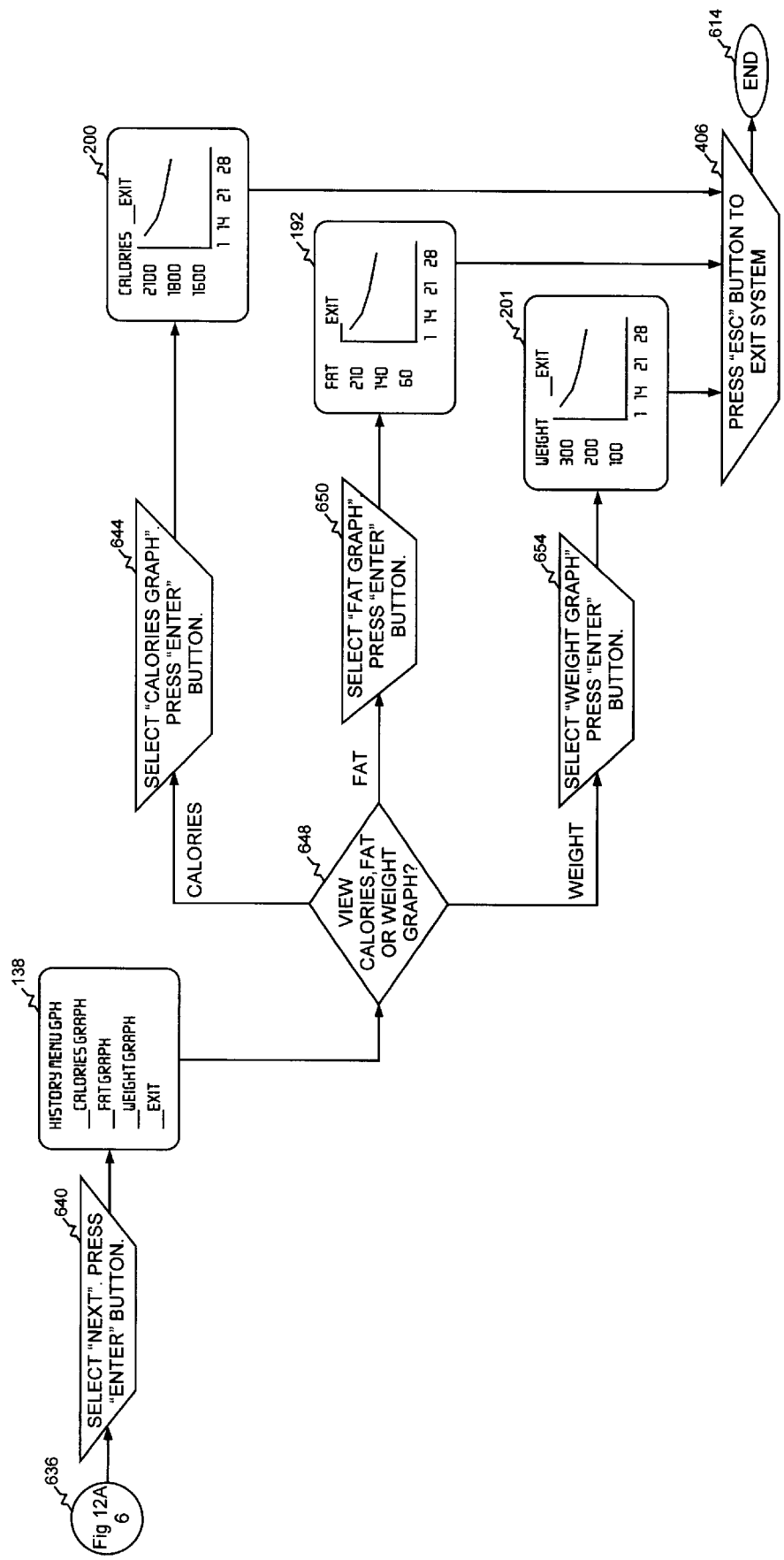

| | |
|---|---|
| | press enter button |
| 635 | Output to FIG. 12B item 6 |
| 636 | Input from FIG. 12A item 6 |
| 640 | Action, select "next" (history menu) press enter button |
| 644 | Action, select "calories graph", press enter button |
| 648 | Decision, view calories, fat, or weight graph? |
| 650 | Action, select "fat graph", press enter button |
| 654 | Action, select "weight graph", press enter button |

SUMMARY

The personalized hand held calorie computer is an interactive personal nutrition and exercise management system contained in a hand held computer. This system is capable of keeping in memory storage extensive food listings with associated calorie and fat content and exercise listings with associated calorie burning rates. The user can view food calorie and fat data or input it when he/she consumes it. A built in receiver in the unit allows the user to utilize various optional wireless activity sensing devices and bicycle odometers equipped with transmitting devices already on the market to automatically input burned calories while performing the exercise or activity. Exercises can also be entered manually. The user's personal data such as age, sex, weight, height and lifestyle which he/she enters into the system is used to calculate suggested weight, daily target calories and fat, daily calorie output, and exercise burning rates. Weight, caloric/fat input and caloric output status can be viewed in chart and graph form on a daily basis or historically over several week periods. The system can be programmed to accommodate special medical or athletic diet requirements such as that for diabetics or marathon runners. Alarms warn the user when he/she is approaching his/her daily caloric/fat targets. Alarms can also be set by the user on a one-time or recurring basis for personal or medical reasons such as for taking medications. Access to the system is password protected for the user's confidentiality. The personalized hand held held calorie computer will be available in various languages.

DESCRIPTION—FIG. 1

A typical embodiment of our unique interactive personalized hand held calorie computer designed to be used by anyone wishing to lose weight; gain weight or maintain a certain diet for personal, athletic or medical reasons by tracking calories and fat consumed and calories burned through normal lifestyle and exercises based on the individual's personal characteristics; goals; and lifestyle, is illustrated in FIG. 1 (perspective view). Item 30 is a hand held computer case containing therein a standard hand held electronic computer having the usual data processing circuitry, math coprocessing circuitry, ROM, RAM, LCD, and receiving unit for optional activity sensing and odometer attachments. Typical hand held computers of this type are manufactured by Casio (BOSS Organizer, 128KB model SF-7900) and Sharp (128KB Organizer, model Y0370).

Our uniquely innovative interactive personalized hand held calorie computer utilizes an alphabetical keyboard 56 containing a plurality of contacts which shift to include numbers 0 through 9, mathematical functions, and punctuation marks. It is our intent that these and the following listed contacts be arranged or labeled in varied configurations according to manufacturers' design.

Shown in FIG. 1 is shift contact 46 which enables the user to switch keyboard contacts 56 between the alphabetical and the secondary functions listed in the last paragraph. The space contact 48 allows the user to insert spaces when entering data into the computer. The directional arrow contacts 50 allow the user to scroll in four directions as indicated by the switch. The menu contact 44 causes the main menu to appear in the liquid crystal display (LCD) 54. The enter contact 32 which allows data to be stored in specific screens also allows activation of menu, next, more and exit selections. The delete contact 34 deletes specified data already stored. Reset contact 36 acknowledges alarms and stops alarm audible signal, resets the timer, activity sensing device and odometer. Start/stop toggle switch 38 starts and stops the timer, activity sensing device and odometer. The calories retrieval contact 40 allows direct access to up-to-the-minute caloric status. The on/off contact 42 turns the unit's power on and off and the esc contact 52 allows the user to instantly exit the system.

OPERATIONS FIG. 2

Figure 2:
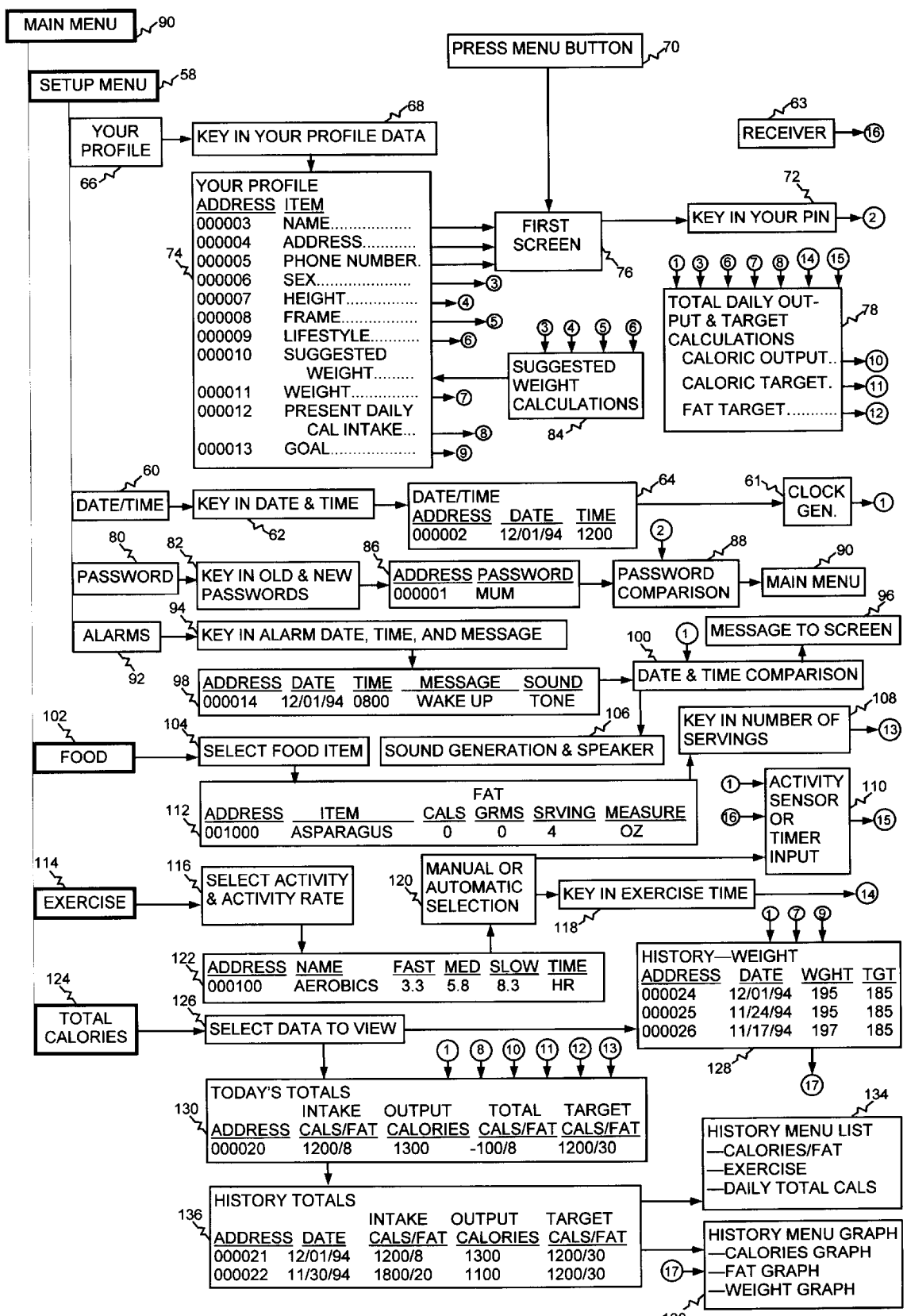
FIG. 2 is a block diagram showing the interrelationships between all the features and functions of the personalized hand held calorie computer.

FIG. 2 is a system diagram/flow chart which shows the relationship between the various functions of the Personalized Hand Held Calorie Computer. To gain access to the main menu the user presses the menu button 70. The first screen 76 has a place to enter the password and the statement "If found call" with the name and phone number of the user or the statement "If found mail to" and the user's mailing address. The phone number and address information for the first screen is provided from your profile 74 data. When the user enters the PIN, block 72, and presses the enter button 32 it is compared with the password, block 88, in memory, block 86. If there is a match the main menu screen 90 appears. To change the password the user selects setup, block 58, in the main menu and presses the enter button 32 and selects password, block 80, and press the enter button 32 in the setup menu to gain access to the password screen 164. In the password screen the user keys in the old and new passwords, block 82, and presses the enter button 32 to change the password in RAM, block 86. To enter or change the date and time select date/time, block 60, at the main menu, key in desired date and time, block 62, at the date and time screen 144 to enter the data into RAM, block 64. That resets the system clock 61. To enter or change personal profile data select set up, block 58 in the main menu and press the enter button 32 and select your profile, block 66, in the setup menu and press the enter button to gain access to first personal profile screen. Data requested may be entered or changed, block 68. Pressing the enter button 32 will give the user access to the next personal profile until all 8 screens have been accessed. Exit from the system is accomplished by pressing the esc button 52. Selecting exit at any screen and pressing the enter button 32 returns the user to the previous screen. Sex, height, frame and lifestyle data in your profile, block 74, are fed into the suggested weight calculations, block 84, to derive a suggested weight which is displayed in the goal screen 178, of your profile, block 74. The user can set one time and recurring alarms by selecting setup 58, and pressing the enter button 32 and selecting alarms, block 92, in the setup menu and pressing the enter button 32. He/she then keys the desired alarm date, time, and message block 94 to store in RAM, block 98. The date and time are compared, block 100, with an input from the date/time clock, block 61. When there is a match the sound generation circuit is activated which in turn feeds the speaker, block 106, and the message appears on the screen 96. The alarm is turned off by depressing the reset button 36. To view or enter food consumed the user selects food, block 102, in the main menu and presses the enter button 36. He/she can then select the food item, block 104, to retrieve food items from RAM, block 112. To make an entry of food which has been consumed the user then keys in the fraction or number of servings, block 108, and presses the enter button 32. These calories/fat associated with this entry are stored in memory under todays totals, block 130. To view or enter an exercise manually or automatically using the timer or optional pedometer/odometer attachments the user selects exercise, block 114, in the main menu and presses the enter button 32. He/she selects the activity, block 116, to retrieve activity from RAM, block 122. If the user selects manual operation, block 120 he/she enters the rate and the time, block 118, of the exercise and presses the enter button 32. For automatic operation he/she uses the built in timer or wireless activity sensor input, block 110 from the receiver 63. The manual and automatic exercise data is fed to the total daily output and target calculations, block 78, where it is used along with personal profile data to derive appropriate caloric/fat targets and caloric output information which in turn is stored under today's totals, block 130. The user may view current caloric/fat intake and exercise caloric output totals, block 130, by pressing the calories button, block 40, and going through the password screen. If he/she wishes to view historical data he/she selects total calories, block 124, in the main menu and presses the enter button 32. In the total calories menu screen 194 the user selects data to view, block 126, and presses the enter button 32. The user may then select history weight, block 128, from personal profile data or history calories, exercise, daily total calories, calories graphs, fat graphs and weight graphs from history totals in RAM, block 136 to gain access to historical charts (Calories/fat, Exercise and Daily Total Calories), block 134, and historical graphs (input Calories, input Fat and Weight), block 138. The date from the date/time, block 61, and present daily calorie intake from your profile, block 74, is the last of the data needed by today's totals, block 130, to produce the historical data. The History weight chart gets data from the date/time generator 61, the user's weight and goal from your profile data 74.

OPERATIONS FIG. 3

Figure 3:
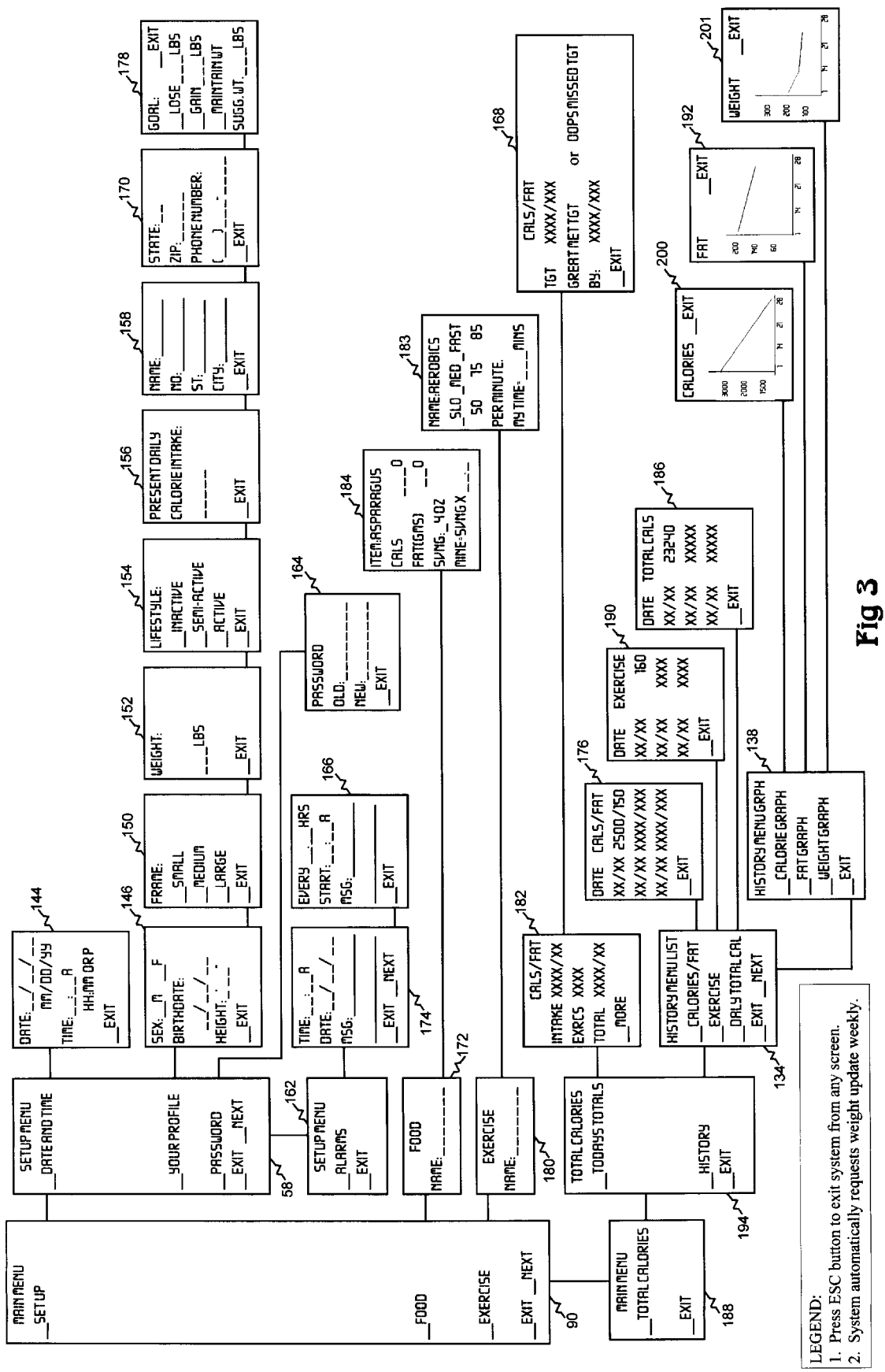
FIG. 3 is a block diagram of the hand held calorie computer's menu system showing how the menu driven concept operates in this invention.

The ECC Menu system shown in FIG. 3 shows the paths taken for the selection of the personalized hand held calorie computer functions. To set or reset the date and or time the path is from the main menu 90 to the setup menu 58 to the date/time set up screen 144. To enter or change the personal profile the path is from the main menu 90 to the setup menu 58 to the sex/birth date/height screen 146 to the frame screen 150 to the weight screen 152 to the lifestyle screen 154 to present daily calorie intake screen 156 to name/address screen 158 to the state/phone screen 170 to the goal screen 178. To enter or change the PIN the path is from the main menu 90 to the setup menu 58 to the password screen 164. To set, change or delete alarms the path is from the main menu 90 to the set up menu screen one 58 to the setup menu screen two 162 to the one time alarm screen 174 to the recurring alarm screen 166. To view or enter food items consumed the path is from the main menu 90 to the food screen 172 to the food item entry/view screen 184. To enter or view exercise the path is from the main menu 90 to the exercise screen 180 to exercise entry/view screen 183. To view current calories status the path is from the main menu screen one 90 to the main menu screen two 188 to the total calories screen 194 to todays totals screen 182 to target screen 168. To view historical calories/fat consumed chart the path is from the main menu screen one 90 to the main menu screen two 188 to the total calories screen 194 to the history menu 134 to the calories/fat chart screen 176. To view historical exercise calories output chart the path is from the main menu screen one 90 to the main menu screen two 188 to the total calories screen 194 to the history menu 134 to the exercise chart screen 190. To view historical daily total calories chart the path is from the main menu screen one 90 to the main menu screen two 188 to the total calories screen 194 to the history menu 134 to the daily total calories chart screen 186. To view historical calories consumed graph, the path is from the main menu screen one 90 to the main menu screen two 188 to the total calories screen 194 to the history menu screen one 134 to the history menu screen two 138 to the calories graph screen 200. To view historical fat consumed graph the path is from the main menu screen one 90 to the main menu screen two 188 to the total calories screen 194 to the history menu screen one 134 to the history menu screen two 138 to the fat graph 192. To view historical weight graph the path is from the main menu screen one 90 to the main menu screen two 188 to the total calories screen 194 to the history menu screen one 134 to the history menu screen two 138 to the weight graph screen 201.

OPERATIONS FIGS. 6, 7, 7A

The flowchart shown in FIG. 6 shows the steps to set or reset the standard clock and calendar programs in the date and time subsystem. The sequence begins with flowchart start symbol 376. Depressing the menu button 70 brings up the first screen 76. This screen may also contain the owner's name phone number and address if desired for identification purposes in case the unit is lost. When the correct password is entered, block 72, and the enter button is depressed, block 386 the main menu 90 appears on the LCD. The user selects setup and presses the enter button, block 390. He/she selects date and time from the setup menu screen 58, and presses the enter button, block 394. When the date/time screen 144 appears the user keys in the desired date and time, block 62, and presses the enter key, block 386, to store the information. To leave the date/time subsystem the user presses the esc button, block 406 which leads to flowchart end symbol 408.

FIGS. 7 and 7A flowcharts show the steps necessary to set or reset the personal profile data collection screens from which suggested weight, target weight, daily input caloric/fat targets, metabolic rate, exercise caloric burning characteristics and graduated daily caloric targets are derived. The flowchart sequence begins with oval flowchart start symbol 409. To enter the personal profile in the computer the user presses the menu button, block 70. When the first screen 76 appears he/she enters the password, block 72, and presses the enter button, block 386. At the main menu 90 he/she selects setup and presses the enter button, block 390. The user then selects your profile and presses the enter button, block 420, from the setup menu 58. He/she keys in his/her sex, birth date, and height, block 424, at the sex/birth date screen 146 and presses the enter button, block 386. From the frame screen 150 he/she selects his/her frame size and presses the enter button, block 432. Next, the user keys in his/her weight, block 436, in the weight screen 152 and presses the enter button, block 386. When the lifestyle screen 154 appears the user selects his/her lifestyle and presses the enter button, block 444. When the present daily calorie screen 156 appears he/she enters his/her present calorie intake, block 448. Flowchart continuation symbol 451 labeled "FIG. 7A, 5" takes sequence into FIG. 7A where it is picked up with flowchart continuation symbol 452 labeled "FIG. 7, 5".

At FIG. 7A after the calorie intake is keyed in the enter button is pressed, block 386. When the name/address screen 158 appears he/she may enter his/her name, street number, street name, and city, block 456, (if he/she wishes the information to show in the password screen) and presses the enter button, block 386. When the state/phone screen 170 appears he/she keys in his/her state, zip code, phone number, block 464, (if he/she wishes the information to show in the password screen) and presses the enter button, block 386. When the goal screen 178 appears he/she selects his/her goal (lose x amount of pounds, gain x amount of pounds or maintain) and presses the enter button, block 472. At this point the computer calculates and presents a suggested target weight based on the user's personal profile. The user is free to accept the suggested weight target or to establish his/her own weight target. The computer will use whatever goal figures are entered to establish future weight targets. This completes the entering of the personal profile data. To exit the system press the esc button, block 406. Oval end flowchart symbol 474 stops the flowchart sequence.

OPERATIONS FIGS. 8, 9, 10

Figure 8:
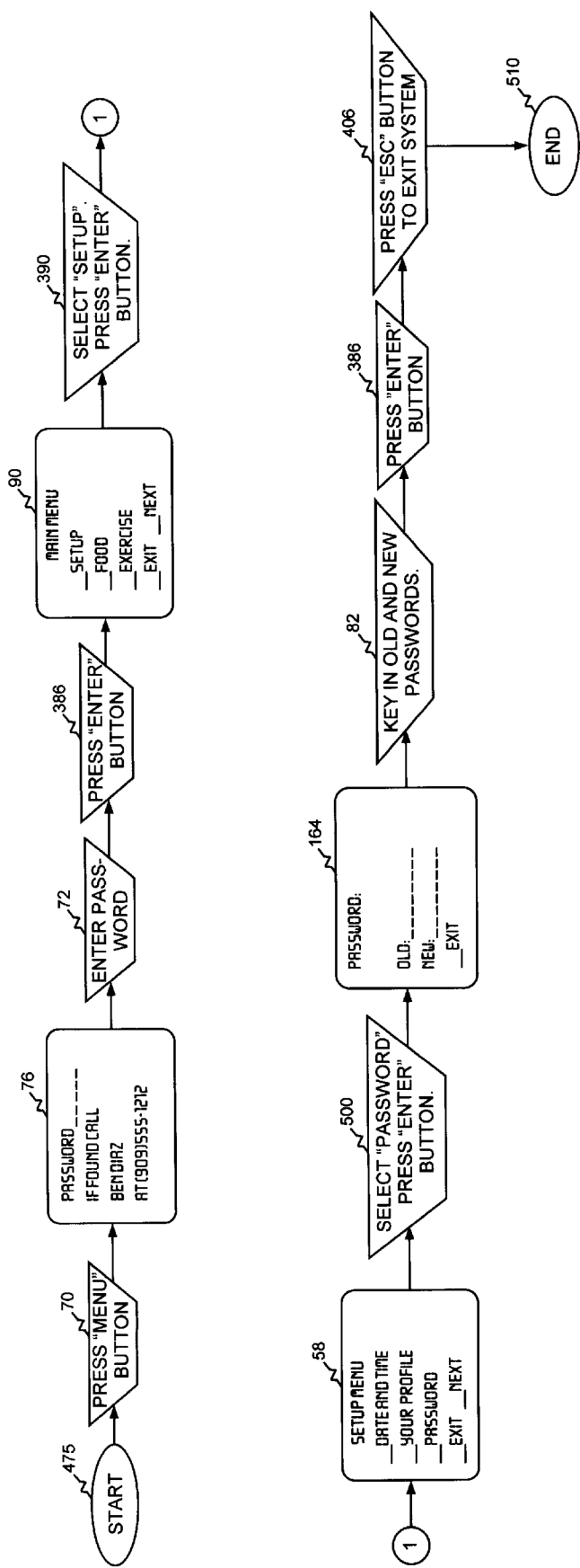
FIG. 8 is a flowchart showing the steps taken to set or reset the personal identification number in the personal hand held calorie computer.

FIG. 8 is a flowchart for steps to enter or change the personal identification number. Oval start flowchart symbol 475 begins the flow chart sequence The user presses the menu button, block 70, to access the main menu. At the first screen 76 the user enters the password, block 72, which can be up to 5 digits long and presses the enter button, block 386. The correct password allows access to the main menu. At the main menu screen 90 the user selects setup and presses the enter button, block 390. At the setup menu screen 58 the user selects password and presses the enter button, block 500, to access the password subsystem. In the password screen 164 the user enters the old and new passwords, block 82 and presses the enter button, block 386. To exit from the password mode the user presses the esc button, block 406. Oval end flowchart symbol 510 stops the sequence.

Figure 9:
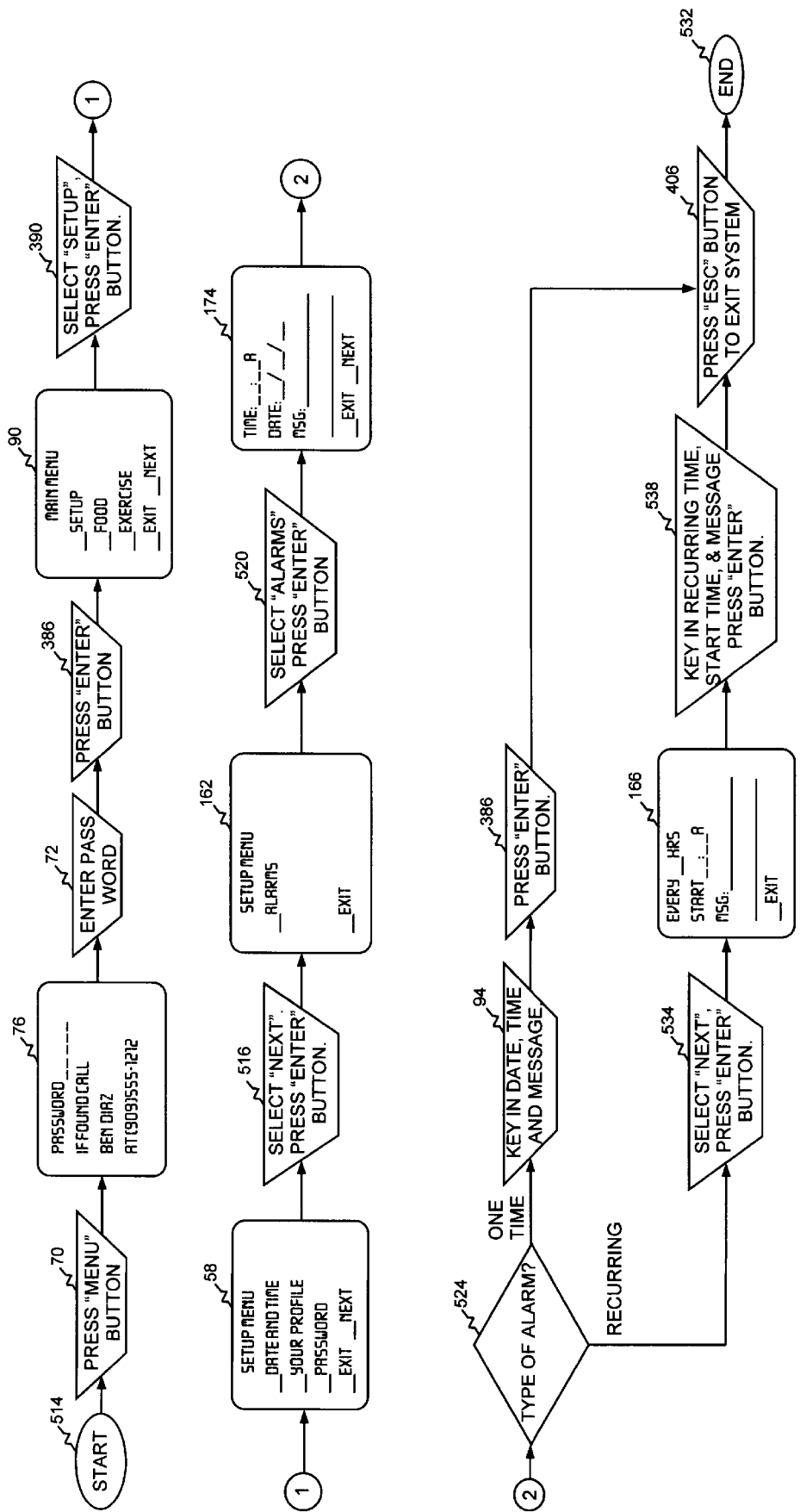
FIG. 9 is a flowchart showing the steps taken to set alarms in the personal hand held calorie computer.

FIG. 9 is a flowchart outlining the steps necessary to set, reset and delete alarms. Oval start flowchart symbol 514 begins the sequence. The process begins the same as the others listed previously—by pressing the menu button, block 70, which takes the user through the first screen 76 to the main menu screen 90 if the PIN is accepted. At the main menu he/she selects setup and presses the enter button, block 390. In the setup menu screen 58 he/she selects next and presses the enter button, block 516. From the setup menu screen two 162 alarms is selected and the enter button is pressed, block 520, to access the alarm subsystem. By answering "type of alarm?" decision 524 he/she chooses whether to use a one time alarm or an alarm that is set to provide a signal on desired intervals. If the user wishes to set, reset or delete a one time alarm he/she enters the time, date and message, block 94 in the first alarm screen 174 and presses the enter button, block 386. To exit the user presses the esc button, block 406. If the user wishes to set, reset or delete a recurring alarm he/she selects next and presses the enter button, block 534, while in first alarm screen 174. In the recurring alarm screen 166 the user enters interval hours, first alarm time and message and presses the enter button, block 538. To exit the system he/she presses the esc button, block 406. Oval end flowchart symbol 532 stops the sequence.

Figure 10:
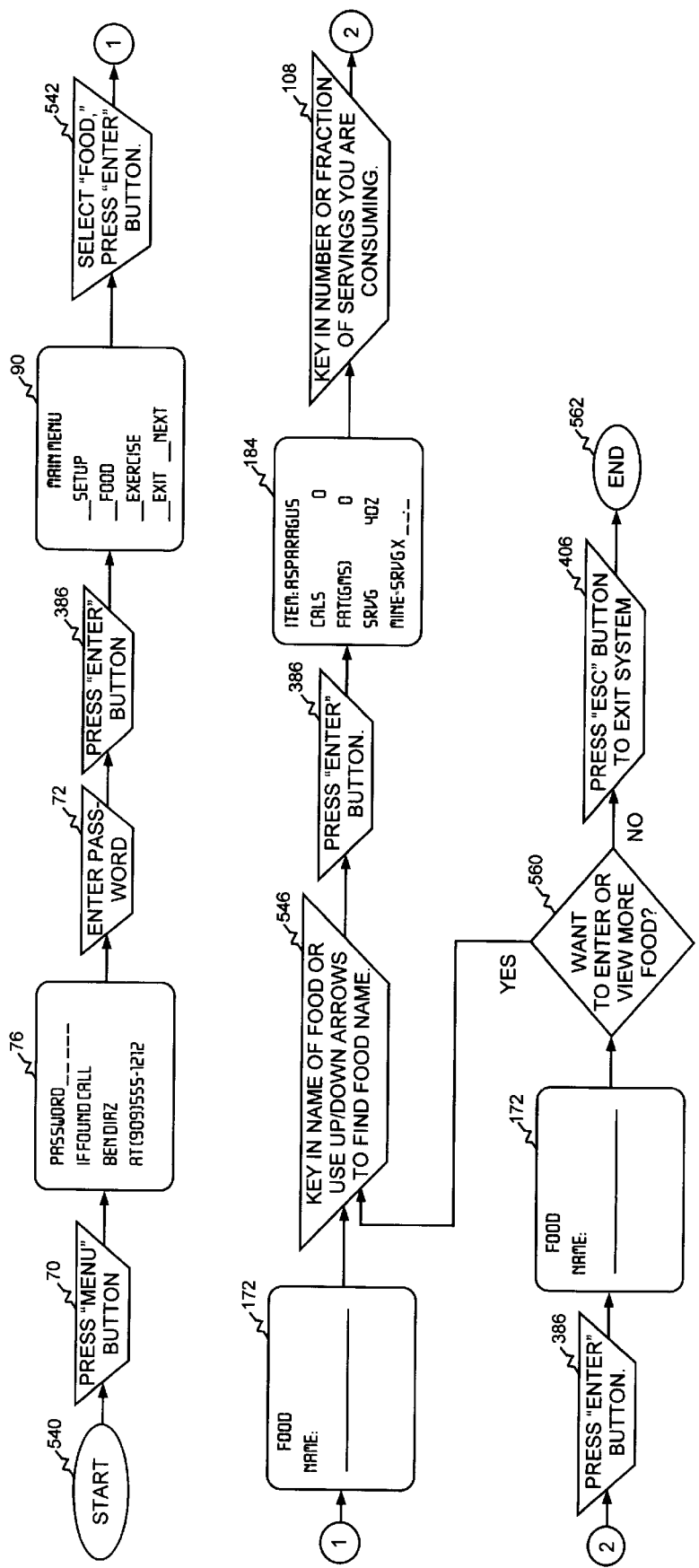
FIG. 10 is a flowchart showing the steps taken to view and or enter food consumed in the personal hand held calorie computer.

FIG. 10 is a flowchart showing the steps taken to enter food items consumed or view food items before consumption. Oval start flowchart symbol 540 begins sequence. The user presses the menu button, block 70 for access to the system. When the first screen 76 appears the user enters his/her password, block 72 and presses the enter button, block 386. If the password is accepted the main menu screen 90 appears. At the main menu screen the user selects food and presses the enter button, block 542. When the food screen 172 appears the user may either key the food name or use the up/down arrows to scroll to the food item, block 546 and presses the enter button, block 386. To enter food consumed the user keys in the number or fractions of servings, block 108, and presses the enter button, block 386. The food screen 172 will reappear. If the user wishes to view or enter other food items he/she answers yes to "want to enter or view more food?" decision 560 and keys in or scrolls to the food items, block 546, and presses the enter button, block 386. He/she can again key in the number or fraction of servings, block 108 and press the enter button, block 386, to enter the food item into the system. If the user does not wish to view or enter anymore food items he/she presses the esc button to exit the system, block 406. Oval end flowchart symbol 562 stops the sequence.

OPERATIONS FIGS. 11, 12, 12A, 12B

Figure 11:
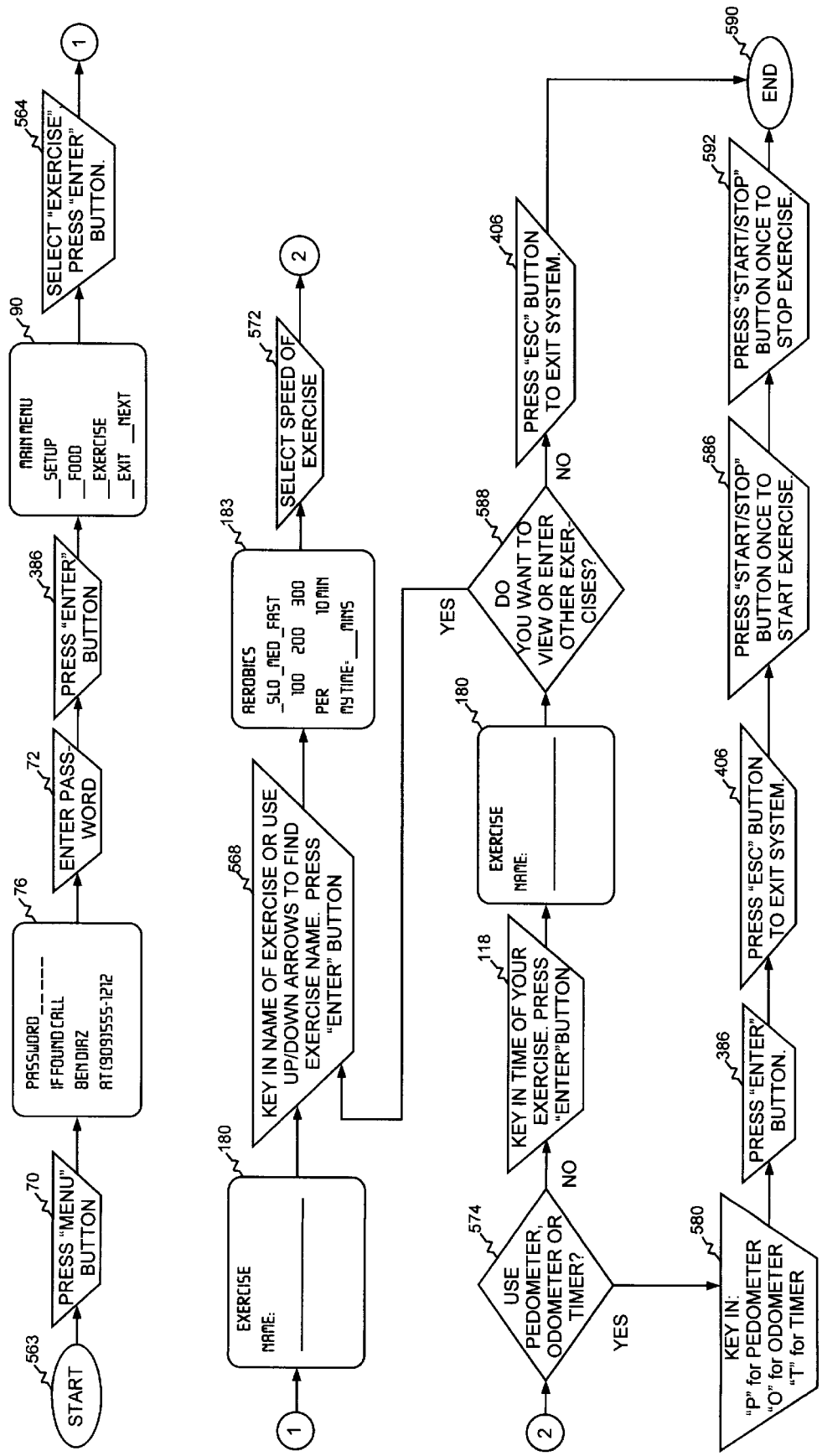
FIG. 11 is a flowchart showing the steps taken to view and or enter exercises performed in the personal hand held calorie computer.

FIG. 11 shows a flowchart to view or enter exercises. Oval start flowchart symbol 563 begins sequence. The user presses the menu button, block 70, to get the first screen 76 in which he/she enters his/her password, block 72, and presses the enter button, block 386. If the password is accepted the main menu 90 appears. In the main menu the user selects exercise and presses the enter button, block 564. At the exercise screen 180 the user may key in the exercise name or scroll up/down to it and press the enter button, block 568. At the selected exercise screen 183 the user selects the speed of the exercise, block 572. Manual or automatic input decision is made by answering "use pedometer, odometer, or timer?" decision 574. If the user has already performed the exercise and only wishes to enter it he/she then keys in the time duration of the exercise and presses the enter button, block 118. The blank exercise screen 180 will reappear. To view or enter other exercises the user answers "do you want to view or enter other exercises?" decision 588. If the user wishes to view or enter another exercise he/she may either key in or scroll to the exercise and press the enter button, block 568. At the selected exercise screen the user again selects the speed of the exercise, block 572; keys in the time duration of the exercise; and presses the enter button, block 118. To exit the system the user presses the esc button, block 406. If the user wishes to use the timer, an activity sensing device or the odometer attachments instead of entering the time duration of the exercise he/she enters "T" for timer, "P" for pedometer or "O" for odometer,block 580, and presses the enter button 32. To exit the system he/she presses the esc button, block 406. To activate the exercise interactive mode press the start/stop button one time, block 586. To stop the exercise interactive mode and enter the data into the system he/she presses the start/stop button one more time, block 592. Oval end flowchart symbol 590 stops the sequence.

FIGS. 12, 12A 12B are a flowchart showing the steps the user must take to view his/her daily and historical weight, fat intake, caloric intake, caloric output, and target data in the form of charts and graphs. To enter this mode the user can use the quick method or the conventional method. To use the conventional method begin with oval start flowchart symbol 593. He/she presses the menu button, block 70. When the first screen 76 appears he/she keys in the PIN, block 72 and presses the enter button, block 386. If the PIN is accepted the first main menu screen 90 appears. The user then selects next and presses the enter button, block 516. At the second main menu screen 188 he/she selects total calories and presses the enter button, block 598. To select today's or historical data answer "today's totals or history?" decision 602. At the total calories screen 194, if the user wishes to view the current data he/she selects todays totals and presses the enter button, block 604. This brings up the current cals/fat intake screen number one 182. Flowchart continuation symbol 605 labeled "FIG. 12A, 4" connects FIG. 12 to flowchart continuation symbol 607 labeled "FIG. 12, 4". To see if he/she is meeting current caloric/fat intake targets he/she selects more and presses the enter button, block 608. If the user has met his/her targets the answer to "met target?" decision 610 is yes and the target met screen 612 appears. If the user has not met the target the answer to "met target?" decision 620 is no and the missed target screen 616 appears. To exit the system he/she presses the esc button, block 406.

To use the quick method begin with oval start flowchart symbol 594. Pressing the calories button, block 596, takes the user directly through the password screen to the current cals/fat intake screen number one 182. To view if he/she is meeting his/her current cal/fat intake target the user selects more and presses the enter button, block 608. If the user has met his/her targets the answer to "met target?" decision 610 is yes and the target met screen 612 appears. If the user has not met the target the answer to "met target?" decision 620 is no and the missed target screen 616 appears. When the user wishes to exit the system he/she presses the esc button, block 406.

Flowchart continuation symbol 606 labeled "FIG. 12A, 5" connects to FIG. 12 flowchart continuation symbol 617 labeled "FIG. 12, 5". At the total calories screen 194 he/she then selects history and presses the enter button, block 618, to view his/her historical data. The user decides whether to view charts or graphs by answering "view charts or graphs?" decision 622. To view historical calories/fat intake chart the user chooses calories/fat at "view calories/fat, exercise, or daily total calories?" decision 628 and selects calories/fat and presses the enter button, block 624, at the history menu 134. This brings up the cals/fat chart screen 176. To view the historical calories output chart the user chooses the exercise path when he/she selects exercise and presses the enter button, block 630 at the history menu 134. This brings up the exercise chart screen 190. To view historical daily total calories (intake minus output) chart the user takes that path at decision 628 when he/she selects daily total cals and presses the enter button, block 634, at the history menu 134. This brings up the daily total calories (intake minus output) chart 186. To exit the user presses the esc button, block 406. When the user selects historical graphs at the history menu 134 he/she is choosing to view the graphs at the "view charts or graphs?" decision 622. Flowchart continuation symbol 635 labeled "FIG. 12B, 6" connects flowchart FIG. 12A to FIG. 12B flowchart symbol 636 labeled "FIG. 12A, 6". To access the historical graphs the user selects next and presses the enter button, block 640. When the second screen of the history menu 138 appears he/she answers to the "view calories, fat, or weight graph?" decision 648 to view the historical calories intake, fat intake, or weight graph. To view the historical calories intake graph screen 200 the user selects calories graph and presses the enter button, block 644. To view the historical fat intake graph the user selects fat graph and presses the enter button, block 650. This brings up the fat graph screen 192. To view the historical weight graph the user selects weight graph and presses the enter button, block 654. This brings up the weight graph screen 201. To exit the system from any of the graphs the user presses the esc button, block 406. Oval end flowchart symbol 614 stops the sequence.

OPERATIONS FIGS. 4, 4A

FIG. 4 is a flowchart showing the formula for women's suggested weight. The flow chart utilizes the user's sex, frame size, height and lifestyle from the data inputted into the personal profile applied to 8 basic formulas to derive the individual's suggested weight. The easiest way to demonstrate this flow chart is to work through various hypothetical situations. The first situation is a 22 year old 4 foot 11 inch female with a small frame, living an inactive lifestyle. The chart begins with the oval start symbol 204. The answer to "1female?" decision 212 is yes. The answer to "1small frame?" decision 206 is yes. The answer to "1inactive lifestyle?" decision 218 is yes. The answer to "1height=or >5 feet?" decision 226 is no, so the calculation for this person is 1.67×height in inches+number of years over age 30=7suggested weight 250. Inserting the values in the formula; 1.67×59+0 yields a suggested weight of 98.53 pounds.

If this person were 5 feet and one inch tall the answer to "1height=or >5 feet?" decision 226 would then be yes and the calculation would be 100+(4.07×number of inches over five feet)+(0.5×number of years over 30)=2suggested weight 240. Substituting values; 100+(4.07×1) +(0.5×0)= 104.07 pounds suggested weight.

If this same person led an active lifestyle it would change the answer of "1inactive lifestyle?" decision 218 to no. The answer to "1active lifestyle?" decision 225 is yes. The answer to "2height=or >5 feet?" decision 232 remains yes, so the formula changes to: 100+(4.452×number of inches over 5 feet)+(0.5×number of years over age 30)=3suggested weight 244. Inserting values in the calculation; 100+(4.452× 1)+(0.5×0)=104.452 pounds suggested weight.

If she leads a semi-active lifestyle, is 35 years old, and is 4 feet 11 inches tall the answer to "1active lifestyle?" decision 225 is no. The answer to "3height=or >5 feet?" decision 220 is no. The calculation is: 1.67×height in inches+number of years over age 30=7suggested weight 250. Substituting values; 1.67×59+5=103.53 pounds suggested weight.

If the above user were five feet one inch tall the answer to "3height=or >5 feet?" decision 220 changes to yes. The calculation used becomes: 100+(4.32×number of inches over five feet)+(0.5×number of years over age 30)= 1suggested weight 214. Substituting values: 100+(4.32×1) +(0.5×5)=106.82 pounds suggested weight.

If she has a medium frame and has an active lifestyle the answer to "1small frame?" decision 206 is no. The answer to "large frame?" decision 208 is no. The answer to "2inactive lifestyle?" decision 222 is no. The answer to "2active lifestyle?" decision 228 is yes. The answer to "4height=or >five feet?" decision 236 is yes. The calculation used is: 100+(5×number of inches over five feet)+(0.5×number of years over age 30)=4suggested weight 246. Substituting values; 100+(5×1)+(0.5×5)=107.5 pounds suggested weight.

If this 35year old 4 foot 11 inch female has a medium frame and leads a semi-active lifestyle the answer to "1small frame?" decision 206 is no. "The answer to "1large frame?" decision 208 is no. The answer to "2inactive lifestyle?" decision 222 is no. The answer to "2active lifestyle?" 228 is no. The answer to "2height=or >5 feet? "decision 232 is no.

The calculation is now: 1.67×height in inches+number of years over age 30=7suggested weight 250. Substituting values: (1.67×59inches)+5 =104 pounds suggested weight.

If this same female leads an active lifestyle the answer to "1small frame?" decision 206 is no. "The answer to "1large frame?" decision 208 is no. The answer to "2inactive lifestyle?" decision 222 is no. The answer to "2active lifestyle?" decision 228 is yes. The answer to "4height=or >5 feet?" decision 236 is no. The calculation is now: 1.67×height in inches +number of years over age 30=7suggested weight 250. Substituting values: (1.67×59 inches)+5=104 pounds suggested weight.

If this same female leads an inactive lifestyle the answer to "1small frame?" decision 206 is no. The answer to "1large frame?" decision 208 is no. The answer to "2inactive lifestyle?" decision 222 is yes. The answer to "3 height=or >5 feet?" decision 220 is no. The calculation is: 1.67×height in inches+number of years over age 30=7suggested weight 250. Substituting values: (1.67×59 inches)+5=104 pounds suggested weight.

If this 35 year old five foot one inch female has a large frame, instead, and has a semi-active lifestyle the answer to "1small frame?" decision 206 is no. The answer to "1large frame?" decision 208 is yes. The answer to "3inactive lifestyle?" decision 210 is no. The answer to "3active lifestyle?" decision 224 is no. The answer to "7height=or >5 feet?" decision 238 is yes. The calculation is now: 108+(5.28×number of inches over five feet)+(0.5×number of years over age 30)=6suggested weight 248. Substituting values; 108+(5.28×1)+(0.5×5)=115.78 pounds suggested weight.

If her lifestyle becomes active the answer to "3active lifestyle?" decision 224 changes to yes. The answer to "5height=or >5 feet?" decision 230 remains yes and the calculation changes to: 108+(5.98×number of inches over five feet)+(0.5×number of years over age 30)=5suggested weight 242. Substituting values; 108+(5.98×1)+(0.5×5)= 116.48 pounds suggested weight.

If this person, again, changes her lifestyle to inactive the answer to "3inactive lifestyle?" decision 210 changes to yes. The answer to "6height=or >5 feet?" decision 216 remains yes. The calculation is: 100+(5×number of inches over five feet)+(0.5×number of years over age 30)=4suggested weight 246. Substituting values; 100+(5×1)+(0.5×5)=107.5 pounds suggested weight.

If she is 4 feet 11 inches tall, instead, the answer to "6height=or >5 feet?" decision 216 is no. The calculation is: (1.68×height in inches)+number of years over age 30=8suggested weight 252. Substituting values; (1.68×59) +5=104.12 pounds suggested weight.

If this 4 foot 11 inch tall lady changes to a semi-active lifestyle the answer to "3inactive lifestyle?" decision 210 is no. The answer to "3active lifestyle?" decision 224 is yes. The answer to "5height=or >5 feet?" decision 230 is no. The calculation is: 1.68×height in inches)+number of years over age 30=8suggested weight 252. Substituting values: (1.68× 59)+5=104 pounds suggested weight.

If this 4 foot 11 inch tall lady changes to an active lifestyle the answer to "3inactive lifestyle?" decision 210 is no. The answer to "3active lifestyle?" decision 224 is no. The answer to "7height=or >5 feet?" decision 238 is no. The calculation is: 1.68×height in inches+number of years over age 30=8suggested weight 252. Substituting values: (1.68×59) +5 =104 pounds suggested weight.

FIG. 4A is a flowchart showing the calculation for men's suggested weight. The flow chart utilizes the user's sex, frame size, height and lifestyle from the data inputted into the personal profile applied to 8 calculations to derive the individual's suggested weight. The first situation is a 22 year old 4 foot 11 inch male with a small frame living an inactive lifestyle. The answer to "1female?" decision 212 (FIG. 4) is no and forcing the decision path through flow chart continuation symbol 217 labeled "FIG. 4A, 1" to flowchart continuation symbol 253 labeled "FIG. 4, 1" which is the start of FIG. 4A flowchart. The answer to "2small frame?" decision 254 is yes. The answer to "4inactive lifestyle?" decision 260 is yes. The answer to "7height=or >5 feet?" decision 278 is no. The calculation for this person is: 1.77×height in inches+number of years over age 30=15suggested weight 298. Inserting the values in the calculation; 1.77×59 +0 yields a suggested weight of 104.43 pounds.

If this person were 5 feet and one inch tall the answer to "7height=or >5 feet?" decision 278 would then be yes and the calculation would be: 106+(4.9×number of inches over five feet)+(0.5×number of years over 30)=10suggested weight 288. Substituting values; 106+(4.9×1)+(0.5×0)= 110.9 pounds suggested weight.

If his lifestyle is active the answer to "4inactive lifestyle?" decision 260 is no. The answer to "4active lifestyle?" decision 270 is yes. The answer to "8height=or >5 feet?" decision 282 is yes. The calculation is: 106+(5.364×number of inches over 5 feet)+(0.5×number of years over age 30)=12suggested weight 292. Inserting values; 106+(5.364× 1)+(0.5×0)=111.364 pounds suggested weight.

If his lifestyle is semi-active and he is 35 years old the answer to "4active lifestyle?" decision 270 is no. The answer to "9height=or >5 feet?" decision 262 is yes. The calculation is: 106+(5.2×number of inches over 5 feet)+(0.5×number of years over age 30)=9suggested weight 264. Substituting values; 106+(5.2×1)+(0.5×5)=113.7 pounds suggested weight.

If the user is 4 feet 11 inches tall, instead, the answer to "9height or >5 feet?" decision 262 is no. The calculation is: 1.77×height in inches+number of years over age 30=15suggested weight 298. Substituting values; 1.77×59+ 5=109.43 pounds suggested weight.

If he has a medium frame and leads an active lifestyle the answer to "2small frame?" decision 254 is no. The answer to "2large frame?" decision 256 is no. The answer to "5inactive lifestyle?" decision 266 is no. The answer to "5active lifestyle?" decision 274 is yes. The answer to "10height=or >5 feet?" decision 284 is yes. The calculation used is: 106+(6×number of inches over five feet)+(0.5× number of years over age 30)=13 suggested weight 294. Substituting values: 106+(6×1)+(0.5×5)=114.5 pounds suggested weight.

If he changed to an inactive lifestyle the answer to "5inactive lifestyle?" decision 266 is yes. The answer to "9height=or >5 feet" decision 262 is no. The calculation is: 1.77×height in inches+number of years over age 30=15suggested weight 298. Substituting values: (1.77×59) +5=109 pounds suggested weight.

If this same man changes to a semi-active lifestyle the answer to "5inactive lifestyle?" decision 266 is no. The answer to "5active lifestyle?" decision 274 is no. The answer to "8height=to >5 feet?" decision 282 is no. The calculation is: 1.77×height in inches+number of years over age 30=15suggested weight 298. Substituting values: (1.77×59) +5=109 pounds suggested weight.

If he changes to active lifestyle the answer to "5active lifestyle?" decision 274 is yes. The answer to "10height=>5 feet?" decision 284 is no. The calculation is: 1.77×height in inches +number of years over age 30=15suggested weight 298. Substituting values: (1.77×59)+5 =109 pounds suggested weight.

If he is a 35 year old five foot one inch male with a large frame and leads a semi-active lifestyle the answer to "2small frame?" decision 254 is no. The answer to "2large frame?" decision 256 is yes. The answer to "6inactive lifestyle?" decision 258 is no. The answer to "6active lifestyle?" decision 276 is no. The answer to "13height=or >5 feet?" decision 286 is yes. The calculation is now: 115+(6.36× number of inches over five feet)+(0.5×number of years over age 30)=14suggested weight 296. Substituting values: 115+ (6.36×1)+(0.5×5) =123.86 pounds suggested weight.

If his lifestyle is active the answer to "6active lifestyle?" decision 276 is yes. The answer to "11height=or >than five feet?" decision 280 is yes. The calculation is: 115+(7.2× number of inches over five feet)+(0.5×number of years over age 30)=11 suggested weight 290. Substituting values; 115+ (7.2×1)+(0.5×5)=124.7 pounds suggested weight.

If this person, again, changes his lifestyle to inactive the answer to "6inactive lifestyle?" decision 258 is yes. The answer to "12height=or >than five feet?" decision 268 is yes. The calculation changes to: 106+(6×number of inches over five feet)+(0.5×number of years over age 30)=13suggested weight 294. Substituting values; 106+(6×1)+(0.5×5)=114.5 pounds suggested weight.

If he is 4 feet 11 inches tall, instead, the answer to "12height=or >than 5 feet?" decision 268 is no. The calculation is: 1.8×height in inches+number of years over age 30=16suggested weight 300. Substituting values; 1.8×59+ 5=111.2 pounds suggested weight.

If this same man changes to a semi-active lifestyle the answer to "6inactive lifestyle?" decision 258 is no. The answer to "6active lifestyle?" decision 276 is no. The answer to "13height=or >5 feet?" decision 286 is no. The calculation is: 1.8×height in inches+number of years over age 30=16suggested weight 300. Substituting values: (1.8×59) +5=111 pounds suggested weight.

If he changes to active lifestyle the answer to "6active lifestyle?" decision 276 is yes. The answer to "11height=or >5 feet?" decision 280 is no. The calculation is: 1.8×height in inches+number of years over age 30=16suggested weight 300. Substituting values: (1.8×59)+5=111 pounds suggested weight. FIG. 5 shows the total caloric output calculation flowchart. Continuing with the unique personalized and interactive features of the personalized hand held calorie computer the total caloric output calculations are derived using personal profile data, exercise data inputted by the user and direct inputs from optional activity sensors and odometer attachments. The at-rest daily caloric output (DCO) calculation 322 utilizes the user's weight, block 336, and lifestyle, block 334, to produce a figure roughly representing the amount of calories the individual burns performing every day routine. The DCO is also fed into FIG. 5A from FIG. 5 through continuation symbol 330 labeled "FIG. 5A, 2". For a 100 pound active person the basic DCO calculation 322 is: 10.45×weight+760. Substituting values; 10.45×100+760= 1805 DCO. For a semi-active lifestyle the DCO would drop to 1615 calories. An inactive lifestyle would drop the DCO even further to 1425 calories.

The flowchart for FIG. 5 begins with the oval start symbol 301. If the user chooses to key in an exercise the answer to "manual input?" decision 302 is yes. The activity caloric output ACO calculation 303=modified activity caloric value (MACV)×(DCO/1440)×keyed in time (KIT). When MACV calculation 310=[(weight from personal profile, block 314/ 2.2)×activity caloric value (ACV), calculation block 306]/ 60; ACV calculation 306=a figure between 0 and 99 representing how many times more strenuous an activity is than DCO based on one of three levels (Low, medium or fast/ heavy) stored with exercise data; and KIT 316=the time keyed in "my Time" by user while in the particular exercise screen (FIG. 11 item 183). For this example if the user who weighs 100 pounds and leads a semi-active life style performs low intensity aerobic exercise for 30 minutes the ACV is 3. Substituting values for MACV; [(100/2.2)×3]/60=2.27. Substituting values for ACO; 2.27×(1615/1440)×30=76.37 calories expended performing aerobics at slow speed for 30 minutes. This total is stored in the daily total ACO accumulator 320 where it is available for viewing. At midnight each day the ACO is transferred to the total caloric output register 324 where it is added to the DCO.

If the user chooses to use the timer, an activity sensing device or the odometer the answer to "manual input?" decision 302 is no. The input from the timer, block 305 or activity sensing device or odometer transmitter 318 relays data to the receiver 63 which in turn feeds the activity time or pulse to caloric output ACO converter 308 where it is mixed with the MACV from calculation block 310 and the timer input from the system clock, block 305, to produce the ACO. This output also feeds into the daily total ACO accumulator 320. This data is transferred to the total caloric output register 324 and added to DCO. If the user is male the answer to "2female?" decision 326 is no and total caloric output value 328 is transferred to storage beyond the charts end indicated by the end oval symbol 333. If the user is female the answer to "2female?" decision 326 is yes. The women's total caloric output calculation 332 is: total caloric output×0.73 and is transferred to storage through daily caloric output value 328 and the oval end symbol 333.

Figure 5A:
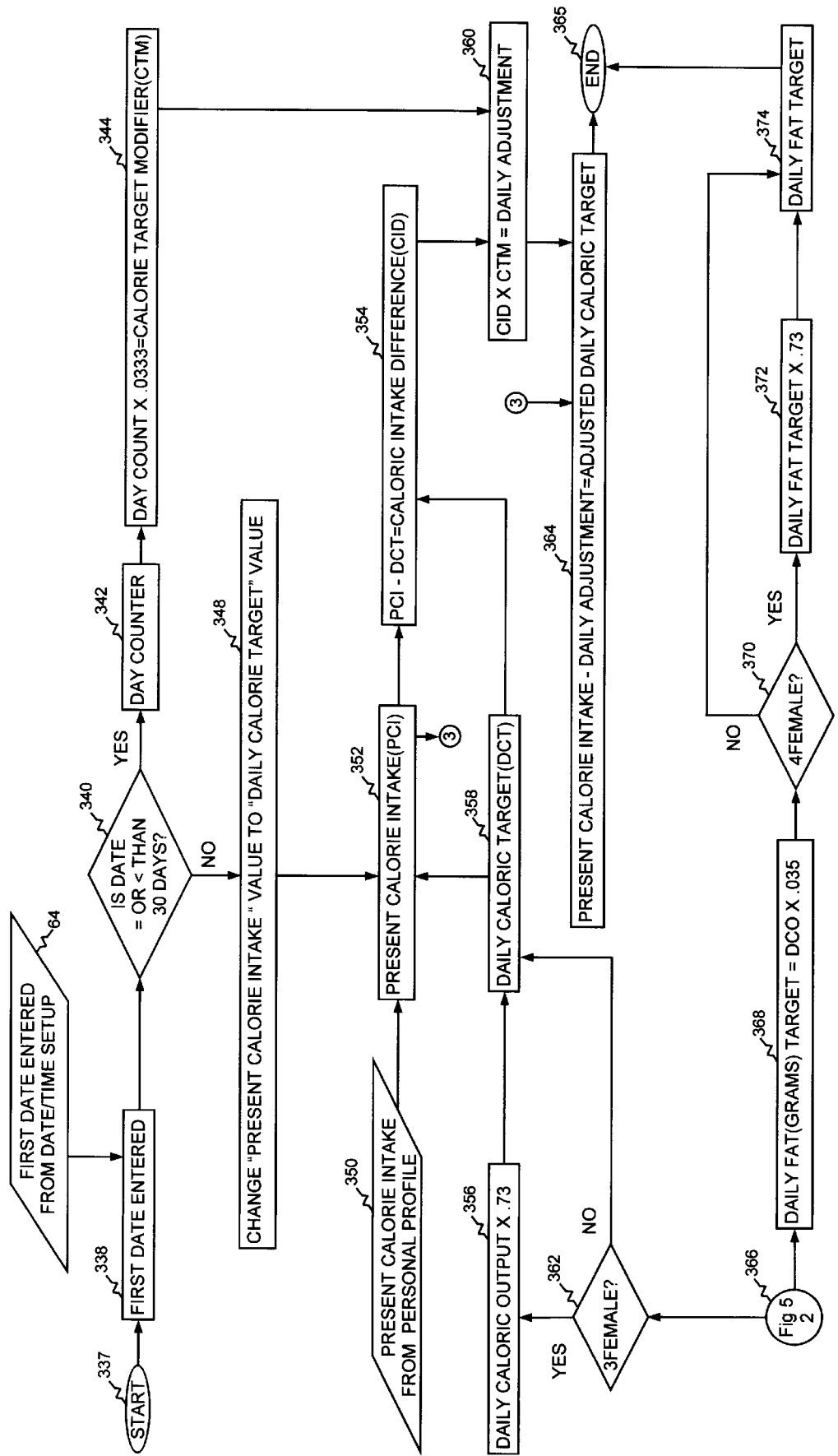
FIG. 5A is a flowchart showing the steps and calculations utilized in deriving the individual's daily caloric and fat input targets.

FIG. 5A is the daily caloric/fat target calculation flowchart which utilizes the user's personal profile data of lifestyle, weight, sex and starting caloric intake to establish a graduated caloric input target the first 30 days and derive a personal caloric input target thereafter. The flowchart begins with the oval start symbol 337. The "first date entered from date/time setup" block 64 goes to "first date entered" register 338 where it is used as a starting reference. This starting reference date is compared with the system calendar date. If the answer to "is date=or <than 30 days?" decision 340 is yes a pulse is fed to the day counter 342 increasing its count by one. Assuming that the user is a 150 pound semi-active female whose starting daily caloric input is 2300 calories and the personalized hand held calorie computer has been in use 10 days. The calculation is: day count×0.0333=calorie target modifier (CTM) 344. Substituting values; 10×0.0333= 0.333 CTM. The DCO of 2137 calories from FIG. 5 is fed through flowchart continuation symbol 366 labeled "FIG. 5, 2" to "3female?" decision block 362 where the answer is yes and women's daily caloric output calculation 356 is used to derive the daily caloric target (DCT) 358. The DCT is subtracted from the present calorie intake (PCI) register 352 to produce a caloric intake difference (CID) value 354 used in the daily adjustment formula 360. In this case the data in the present calorie intake (PCI) register 352 is the present calorie intake from the personal profile 350 data value. Therefore, the value of PCI is now 2300 calories. Substituting values: (2300)−(2137.5×0.73)=739.62×0.333=246.29 daily adjustment. The daily adjustment is subtracted from present caloric intake to derive the adjusted daily caloric target 364. Substituting values; 2300−246.29=2053.71 caloric input target for the 10th day in use which is stored in RAM through the flow chart end symbol 365. If the day count is 31 days the answer to "is date=or <than 30 days?" decision 340 is no. In this case the "change present calorie intake value to daily calorie target value" instruction 348 is triggered causing data in the present caloric intake (PCI) register 352 to be replaced with the daily caloric target (DCT) calculation 358. Therefore, the value of PCI is now 1560.37 calories. Since the DCI and DCT are now the same value the CID equals zero. The calculation is: PCI-(CID ×CTM)=adjusted daily caloric target 360. Substituting value for adjusted daily caloric target; 1560.37-0=1560.37 caloric input target for the 31st day.

Assuming that the user is a 150 pound semi-active male whose starting daily caloric input is 2300 calories and the personalized hand held calorie computer has been in use 10 days. The calculation is: day count×0.0333=calorie target modifier (CTM) 344. Substituting values: 10 ×0.0333=0.333 CTM. The DCO of 2137 calories from FIG. 5 is fed through flowchart continuation symbol 366 labeled "FIG. 5, 2" to "3female?" decision block 362 where the answer is no and the daily target (DCT) 358 is used directly. The DCT is subtracted from the present calorie intake (PCI) register 352 to produce a caloric intake difference (CID) value 354 used in the daily adjustment formula 360. In this case the data in the present caloric intake (PCI) register 352 is the present calorie intake from the personal profile 350 data value. Therefore, the value of PCI is now 2300 calories. Substituting values: 2300-2137=163 daily adjustment. The daily adjustment is subtracted from present caloric intake to derive the adjusted daily caloric target 364. Substituting values: 2300-54=2246 caloric input target for the 10th day in use which is stored in RAM through the flow chart end symbol 365.

To calculate the daily fat target in grams again the DCO is used from FIG. 5. The calculation is: DCO×0.035=Daily fat target(grams) 368. Substituting values; 2137.5×0.035= 74.8 grams. The answer to "4female?" decision 370 is yes. The calculation is: daily fat target×0.73 =women's daily fat target 372. Substituting values; 74.8×0.73=54.6 daily fat target 374 also stored in RAM through flowchart end symbol 365. If the user is a male who also weighs 150 pounds the answer to "4female? " decision 370 is no and the daily fat target calculation is used directly.

Summary, Ramifications, and Scope

Accordingly, the reader will see that the personalized nature of this invention ensures that the user always has a dietary and exercise program specifically tailored to him or her. The user's suggested weight, daily calorie output, exercise activity rate, daily caloric intake targets and daily fat intake targets automatically adjust as he/she inputs changes to his/her goals, weight, and lifestyle. In addition, the optional activity sensing devices and odometer attachments allow the personalized hand held calorie computer to automatically record and update the individual's calories burned while exercising. Furthermore, the personalized hand held calorie computer has the additional advantages in that it permits the user constant access to complete dietary and exercise information in an easy to use hand held computer which would, normally, require cumbersome books; listings; and complicated formulas;

provides the user with personal daily and historical caloric/fat intake, weight and caloric output data in the form of easy to read charts and graphs;

automatically calculates a personal suggested weight specifically based on the user's personal data;

automatically calculates the individual's specific daily caloric output based on his/her personal data;

automatically calculates the individual's specific calorie burning rates based on his/her personal data and the exercise characteristics;

provides quick easy access to food calorie/fat listings from most major restaurant and fast food chain menus in addition to most basic foods;

provides special programming and food listings for unique medical and athletic needs;

provides alarms when the user nears or exceeds his/her daily caloric/fat targets;

provides one time or recurring alarms for personal or medical reasons;

allows the individual to operate his/her personalized hand held calorie computer in complete confidentiality by use of a personal Identification number (PIN);

will be available in English, Spanish, Italian, French, German, and other languages.

Although the description above contains many specifications, these should not be construed as limiting the scope of the invention but as merely providing illustrations of some of the presently preferred embodiments of this invention. For example, the case can have other shapes or configurations such as a unit that opens with the screen and keyboard located on the inside of the covers, a unit that attaches to the wrist, a unit that is small enough to fit in a shirt pocket, etc.

Thus the scope of the invention should be determined by the appended claims and their legal equivalents, rather than by the examples given.

We claim:

1. An interactive personal nutrition and exercise management tool computing device comprising:

(a) a hand held computer case;

(b) a standard electronic computer circuit contained within said computer case, said circuit containing at least a random access memory, a read only memory, a processor and a coprocessor;

(c) a keyboard positioned on said computer case comprising a plurality of standard keyboard buttons including alphabetical characters, numerical characters, predetermined punctuation marks, predetermined mathematical functions, space function, and shift function;

(d) a plurality of standard computer function buttons positioned on said computer case comprising data enter means to store predetermined data in predetermined said random access memory, activation means of predetermined computer functions, a deletion means to remove predetermined data from said random access memory, a reset means to restore predetermined random access memory locations to predetermined values, a menu access means electrically connected to said processor for retrieval of nutrition and exercise menus, a scrolling means electrically connected to said processor to look up screen viewed data in four basic directions, and a quick exit means electrically connected to said processor to initiate instant egress from computer system;

(e) a plurality of special function buttons positioned on said computer case comprising a retrieval means electrically connected to said processor to quickly access predetermined random access memory locations containing predetermined weight, caloric consumption, fat consumption and caloric output data, and a toggle switch means electrically connected to said processor to start and stop predetermined exercise activity measurements;

(f) a liquid crystal display positioned on said computer case with viewing area adequate to present a plurality of graphs, charts, lists and information gathering screens stored in predetermined said random access memory locations;

(g) a receiving means in said computer case electrically connected to said processor to monitor/store signals from a plurality of exercise activity measurement transmitting devices.

2. The nutrition and exercise management tool computing device of claim 1 wherein said plurality of exercise activity measurement transmitting devices externally located from said computer case connected by a wireless communication means to said receiving means to transfer exercise activity data directly to said processor.

3. The nutrition and exercise management tool of claim 1 wherein a suggested weight calculation comprises;

(a) the coprocessor of claim 1 wherein said suggested weight is derived using predetermined said user personal data.

4. The nutrition and exercise management tool of claim 1 wherein a total caloric output calculation comprises;

(a) the coprocessor of claim 1 wherein a daily at rest caloric output, an activity caloric output and a total daily caloric output are derived using predetermined said user personal data; predetermined exercise caloric burning rates and exercise data from said plurality of exercise input means;

(b) the plurality of exercise input means of claim 1 wherein the exercise input is electrically connected to said coprocessor utilizing an activity, timer or pulse to caloric output conversion means, said exercise calorie burning rate, and predetermined said user personal data to derive exercise activity calories burned;

(c) the coprocessor and random access memory of claim 1 wherein said daily at rest caloric output and said exercise activities calories burned are accumulated to provide daily totals;

(d) the coprocessor of claim 1 wherein predetermined said user personal data is used to derive the user's daily intake caloric and fat targets;

(e) a comparison means to provide a plurality of alarm signals when said caloric and fat intake nears or exceeds the target caloric and fat values.

5. The nutrition and exercise management tool of claim 1 wherein a total caloric intake target calculation comprises;

(a) the coprocessor of claim 1 wherein predetermined said user personal data, and a date started is used to derive a graduated daily intake caloric target during a predetermined adjustment period;

(b) the coprocessor of claim 1 wherein predetermined said user personal data is used to derive a daily intake caloric target after said predetermined adjustment period has elapsed.

6. The nutrition and exercise management tool of claim 1 wherein a total fat intake target calculation comprises;

(a) the coprocessor of claim 1 wherein said total fat intake target is derived using predetermined said user personal data.

7. The nutrition and exercise management tool computing device of claim 1 wherein a menu driven means accesses a main menu, a setup menu, nutrition/exercise menus and a plurality of computer program functions.

8. The main menu of claim 7 wherein a nutrition menu with a food list comprises;

(a) a list of predetermined food items and a list of respective calories per serving, fat content per serving and size of serving stored in predetermined random access memory locations;

(b) a food selection means connected to said processor to retrieve a food item and its respective calories and fat content per serving size;

(c) the coprocessor and random access memory of claim 1 wherein the consumed food item calories and fat content are accumulated to provide daily totals.

9. The main menu of claim 7 wherein an exercise menu with a list of exercises comprises;

(a) a list of predetermined exercise activities and respective predetermined calorie burning rates stored in predetermined random access memory locations;

(b) an exercise selection means connected to said processor for retrieval of selected exercise activity with respective calorie burning rate;

(c) a plurality of exercise input means including said receiving means, an internal timer means and a manual means.

10. The main menu of claim 7 wherein a total calories subsystem comprises;

(a) a plurality of daily and historical intake calorie, output calorie, input fat and weight charts and graphs retrieved from predetermined random access memory locations presented on said liquid crystal display on demand.

11. The set up menu of claim 7 wherein a date and time subsystem comprises;

(a) a standard clock and calendar program in the computer case.

12. The set up menu of claim 7 wherein a personal profile subsystem comprises;

(a) a plurality of data collection screens and random access memory locations for collecting a user's personal data including age, sex, height, weight, frame size, lifestyle, weight management goals, and present daily calorie intake.

13. The set up menu of claim 7 wherein a password subsystem comprises;

(a) a plurality of password screens, said random access memory locations, and said keyboard to enter or change said password and;

(b) a comparison means to allow access to the computer system when said password matches a personal identification number entered by the user.

14. The set up menu of claim 7 wherein an alarm subsystem comprises;

(a) a comparison and sound generation means electrically connected to a plurality of alarm input screens, said random access memory, the date and time clock, and said keyboard to provide predetermined audible signals and screen messages when predetermined alarm settings match actual dates and times.

15. In a hand held computer having a standard alpha-numerical keyboard, a plurality of standard computer function buttons, a liquid crystal display with a plurality of lines and character spaces, a plurality of special function buttons to view caloric data and start and stop exercise activity measurement, a random access memory, a read only memory, a central processing unit, a mathematical coprocessor unit, and a plurality of programs to perform required functions, an interactive personal nutrition and exercise management tool computing device comprising;

(a) a menu driven means wherein a main menu, a setup menu, nutrition/exercise menus and said plurality of programs are used to set a password, a date and time clock, a plurality of alarms and to enter a plurality of personal data including a name, a phone number, an address, a sex, an age, a weight, a height, a frame size, a life style and a goal in said random access memory;

(b) said menu driven means wherein said nutrition/exercise menus and said plurality of programs retrieve a food item with its calories and fat content per serving or an exercise activity with its calorie burning rate from a food listing or an exercise listing in said random access memory for presentation on said liquid crystal display;

(c) a plurality of calculation means for producing personalized results including a suggested weight, a caloric input target, a fat input target, a daily at rest calorie output, a modified activity caloric value, an activity caloric output, and a total caloric output using said personal data, said exercise activity inputs, and the clock input;

(d) an accumulation means using the coprocessor and said random access memory to accrue a daily running total of the calories and fat of foods consumed, the calories burned during exercising and a daily caloric output from at rest calculations and to provide a plurality of audible alarms and a plurality of screen messages when the caloric and fat intake nears or exceeds daily said caloric target and or said fat input target;

(e) a status retrieval means for selecting and viewing a plurality of current or historical data including said caloric input, said fat input, said weight, and said caloric output from said random access memory on said liquid crystal display in the form of charts, graphs and other screens formats;

(f) an alarm means for providing a plurality of audible signals and screen messages when the clock output matches the alarm date and time stored in said random access memory;

(g) a wireless receiving means within said hand held computer electrically connected to said central processing unit in such a manner as to convert incoming signals from a plurality of existing wireless remote monitoring devices already in the market comprising of an exercise activity measurement sensor means electrically connected to a wireless transmission means into calories burned in the course of a plurality of activities;

whereby a person can view or enter from extensive food calorie/fat listings as well as personally adjusted weight targets, fat input targets, calorie input targets, and manually or automatically inputted activity calorie burning data tracked and viewed on a daily or historical basis in one compact easy to use hand held computer for the purpose of controlling body weight for personal, medical or athletic reasons.

* * * * *